(12) United States Patent
Behzadi

(10) Patent No.: US 10,660,767 B2
(45) Date of Patent: May 26, 2020

(54) ASSEMBLER FOR MODULAR PROSTHESIS

(71) Applicant: Kambiz Behzadi, Pleasanton, CA (US)

(72) Inventor: Kambiz Behzadi, Pleasanton, CA (US)

(*) Notice: Subject to any disclaimer, the term of this patent is extended or adjusted under 35 U.S.C. 154(b) by 408 days.

(21) Appl. No.: 15/362,675

(22) Filed: Nov. 28, 2016

(65) Prior Publication Data

US 2017/0196706 A1 Jul. 13, 2017

Related U.S. Application Data

(63) Continuation-in-part of application No. 15/202,434, filed on Jul. 5, 2016.
(Continued)

(51) Int. Cl.
*A61F 2/46* (2006.01)
*A61F 2/36* (2006.01)
(Continued)

(52) U.S. Cl.
CPC .......... *A61F 2/4607* (2013.01); *A61B 17/142* (2016.11); *A61B 17/1666* (2013.01); *A61F 2/34* (2013.01); *A61F 2/3609* (2013.01); *A61F 2/3662* (2013.01); *A61F 2/4609* (2013.01); *A61F 2/4637* (2013.01); *A61F 2/4657* (2013.01); *A61B 34/20* (2016.02); *A61F 2/4603* (2013.01); *A61F 2002/30525* (2013.01); *A61F 2002/30565* (2013.01); *A61F 2002/30604* (2013.01); *A61F 2002/30617* (2013.01); *A61F 2002/30718* (2013.01); *A61F 2002/365* (2013.01); *A61F 2002/3611* (2013.01); *A61F 2002/3625* (2013.01); *A61F 2002/3627* (2013.01); *A61F 2002/469* (2013.01); *A61F 2002/4627* (2013.01); *A61F 2002/4629* (2013.01); *A61F 2002/4632* (2013.01); *A61F 2002/4666* (2013.01); *A61F 2002/4671* (2013.01); *A61F 2002/4681* (2013.01);
(Continued)

(58) Field of Classification Search
CPC ............ A61F 2/4607; A61F 2002/4681; A61F 2/4637; A61F 2002/365; A61B 17/1664; A61B 17/1739
See application file for complete search history.

(56) References Cited

U.S. PATENT DOCUMENTS 1,455,621 A 5/1923 Joyner
2,121,193 A 6/1938 Hanicke
(Continued)

FOREIGN PATENT DOCUMENTS

EP 1433445 A1 6/2004
WO 2017029173 2/2017
(Continued)

OTHER PUBLICATIONS

International Search Report for International application No. PCT/US2017/012753, dated May 5, 2017.
(Continued)

*Primary Examiner* — David W Bates
(74) *Attorney, Agent, or Firm* — Patent Law Offices of Michael E. Woods; Michael E. Woods

(57) ABSTRACT

A system and method for improving installation of a prosthesis. Devices include prosthesis installation tools, prosthesis assembly tools, site preparation systems, and improved power tools used in implant site preparation.

32 Claims, 16 Drawing Sheets

Related U.S. Application Data

(60) Provisional application No. 62/277,294, filed on Jan. 11, 2016.

(51) Int. Cl.
*A61F 2/34* (2006.01)
*A61B 17/14* (2006.01)
*A61B 17/16* (2006.01)
*A61F 2/30* (2006.01)
*A61B 34/20* (2016.01)

(52) U.S. Cl.
CPC ............ *A61F 2002/4687* (2013.01); *A61F 2002/4688* (2013.01); *A61F 2002/4694* (2013.01); *A61F 2250/006* (2013.01)

(56) References Cited

U.S. PATENT DOCUMENTS

| | | | |
|---|---|---|---|
| 3,818,514 A * | 6/1974 | Clark | A61F 2/3609 206/438 |
| 4,135,517 A | 1/1979 | Reale | |
| 4,457,306 A | 7/1984 | Borzone | |
| 4,530,114 A | 7/1985 | Tepic | |
| 4,712,951 A | 12/1987 | Brown | |
| 5,108,400 A | 4/1992 | Appel et al. | |
| 5,133,765 A * | 7/1992 | Cuilleron | A61F 2/0095 206/363 |
| 5,318,570 A | 6/1994 | Hood et al. | |
| 5,534,006 A | 7/1996 | Szabo et al. | |
| 5,769,092 A | 6/1998 | Williamson, Jr. | |
| 5,806,518 A | 9/1998 | Mittelstadt | |
| 5,849,015 A * | 12/1998 | Haywood | A61F 2/4607 606/99 |
| 5,980,528 A | 11/1999 | Salys | |
| 6,110,179 A | 8/2000 | Flivik et al. | |
| 6,161,545 A | 12/2000 | Chow | |
| 6,204,592 B1 | 3/2001 | Hur | |
| 6,585,771 B1 * | 7/2003 | Buttermilch | A61F 2/4637 623/21.11 |
| 7,036,211 B1 | 5/2006 | Panks | |
| 8,167,823 B2 | 5/2012 | Nycz et al. | |
| 8,603,100 B2 | 12/2013 | Muller | |
| 9,999,518 B2 | 6/2018 | Mani et al. | |
| 10,251,663 B2 | 4/2019 | Behzadi | |
| 2002/0183851 A1 | 12/2002 | Spiegelberg et al. | |
| 2003/0065398 A1 * | 4/2003 | Cueille | A61F 2/3609 623/22.4 |
| 2003/0229357 A1 * | 12/2003 | Dye | A61F 2/4637 606/99 |
| 2005/0101962 A1 | 5/2005 | Schwenke et al. | |
| 2005/0154398 A1 | 7/2005 | Miniaci et al. | |
| 2006/0015110 A1 | 1/2006 | Pepper | |
| 2006/0142754 A1 | 6/2006 | Irion et al. | |
| 2007/0005144 A1 | 1/2007 | Leisinger et al. | |
| 2007/0162038 A1 | 7/2007 | Tuke | |
| 2009/0192626 A1 | 7/2009 | Keefer et al. | |
| 2010/0249796 A1 * | 9/2010 | Nycz | A61F 2/4609 606/99 |
| 2011/0004318 A1 | 1/2011 | Tulkis et al. | |
| 2011/0178521 A1 | 7/2011 | Siravo et al. | |
| 2011/0264009 A1 | 10/2011 | Walter et al. | |
| 2012/0172939 A1 | 7/2012 | Pedicini | |
| 2012/0209277 A1 | 8/2012 | Leparmentier et al. | |
| 2013/0204264 A1 | 8/2013 | Mani et al. | |
| 2013/0211535 A1 | 8/2013 | Cueille | |
| 2013/0226189 A1 | 8/2013 | Young | |
| 2014/0135773 A1 | 5/2014 | Stein et al. | |
| 2014/0135791 A1 | 5/2014 | Nikou et al. | |
| 2014/0330281 A1 * | 11/2014 | Aghazadeh | A61B 17/60 606/102 |
| 2015/0182350 A1 | 7/2015 | Behzadi | |
| 2015/0182351 A1 | 7/2015 | Behzadi | |
| 2015/0196343 A1 | 7/2015 | Donald et al. | |
| 2015/0201918 A1 | 7/2015 | Kumar et al. | |
| 2015/0282856 A1 | 10/2015 | Haiat et al. | |
| 2016/0166390 A1 * | 6/2016 | Dye | A61F 2/3609 623/23.42 |
| 2016/0206430 A1 * | 7/2016 | Grostefon | A61F 2/3094 |
| 2016/0206433 A1 * | 7/2016 | Grostefon | A61F 2/3607 |
| 2016/0220315 A1 | 8/2016 | Falardeau et al. | |
| 2017/0056205 A1 | 3/2017 | Biegun et al. | |
| 2017/0196506 A1 | 7/2017 | Behzadi | |
| 2017/0196701 A1 | 7/2017 | Behzadi et al. | |
| 2017/0196704 A1 | 7/2017 | Behzadi et al. | |
| 2017/0196705 A1 | 7/2017 | Behzadi | |
| 2017/0196706 A1 | 7/2017 | Behzadi | |
| 2017/0196707 A1 | 7/2017 | Behzadi | |
| 2017/0196708 A1 | 7/2017 | Behzadi et al. | |
| 2017/0196710 A1 | 7/2017 | Behzadi | |
| 2017/0196711 A1 | 7/2017 | Behzadi | |
| 2017/0325972 A1 * | 11/2017 | Steif | A61F 2/4637 |
| 2017/0340456 A1 | 11/2017 | Behzadi | |
| 2018/0049891 A1 | 2/2018 | Termanini | |
| 2018/0235764 A1 * | 8/2018 | Moore | A61F 2/4014 |
| 2018/0235765 A1 | 8/2018 | Welker et al. | |
| 2018/0296364 A1 * | 10/2018 | Harris | A61F 2/4637 |
| 2018/0325695 A1 * | 11/2018 | Wozencroft | A61F 2/4607 |
| 2019/0336307 A1 * | 11/2019 | Sungu | A61F 2/4607 |

FOREIGN PATENT DOCUMENTS

| | | |
|---|---|---|
| WO | 2017029173 A1 | 2/2017 |
| WO | 2018031752 A1 | 2/2018 |

OTHER PUBLICATIONS

Written Opinion of the International Searching Authority for International application No. PCT/US2017/012753 dated May 5, 2017.
International Search Report for International application No. PCT/US2017/046261, dated Oct. 18, 2017.
Written Opinion of the International Searching Authority for International application No. PCT/US2017/046261, dated Oct. 18, 2017.
U.S. Appl. No. 16/276,639, filed Feb. 15, 2019, Kambiz Behzadi.
U.S. Appl. No. 16/278,085, filed Feb. 16, 2019, Kambiz Behzadi.
U.S. Appl. No. 16/278,668, filed Feb. 18, 2019, Kambiz Behzadi.
U.S. Appl. No. 16/374,750, filed Apr. 4, 2019, Kambiz Behzadi et al.
U.S. Appl. No. 16/375,736, filed Apr. 4, 2019, Kambiz Behzadi et al.
U.S. Appl. No. 16/571,180, filed Sep. 15, 2019, Kambiz Behzadi.
U.S. Appl. No. 16/586,960, filed Sep. 28, 2019, Kambiz Behzadi.
U.S. Appl. No. 16/589,099, filed Sep. 30, 2019, Kambiz Behzadi.
U.S. Appl. No. 16/595,341, filed Oct. 7, 2019, Kambiz Behzadi.
U.S. Appl. No. 62/277,294, filed Jan. 11, 2016, Kambiz Behzadi.
U.S. Appl. No. 62/353,024, filed Jun. 21, 2016, Kambiz Behzadi.
U.S. Appl. No. 62/355,657, filed Jun. 28, 2016, Kambiz Behzadi.
U.S. Appl. No. 62/373,515, filed Aug. 11, 2016, Kambiz Behzadi.
U.S. Appl. No. 62/651,077, filed Mar. 31, 2018, Kambiz Behzadi.
U.S. Appl. No. 62/742,851, filed Oct. 8, 2018, Kambiz Behzadi.
U.S. Appl. No. 62/743,042, filed Oct. 9, 2018, Kambiz Behzadi et al.
U.S. Appl. No. 15/202,434, filed Jul. 5, 2016, Kambiz Behzadi.
U.S. Appl. No. 15/234,782, filed Aug. 11, 2016, Kambiz Behzadi et al.
U.S. Appl. No. 15/234,880, filed Aug. 11, 2016, Kambiz Behzadi et al.
U.S. Appl. No. 15/235,032, filed Aug. 11, 2016, Kambiz Behzadi et al.
U.S. Appl. No. 15/235,053, filed Aug. 11, 2016, Kambiz Behzadi.
U.S. Appl. No. 15/284,091, filed Oct. 3, 2016, Kambiz Behzadi.
U.S. Appl. No. 15/396,785, filed Jan. 2, 2017, Kambiz Behzadi et al.
U.S. Appl. No. 15/398,996, filed Jan. 5, 2017, Kambiz Behzadi.
U.S. Appl. No. 15/453,219, filed Mar. 8, 2017, Kambiz Behzadi.
U.S. Appl. No. 15/592,229, filed May 11, 2017, Kambiz Behzadi.
U.S. Appl. No. 15/687,324, filed Aug. 25, 2017, Kambiz Behzadi.

(56) References Cited

OTHER PUBLICATIONS

U.S. Appl. No. 15/716,529, filed Sep. 27, 2017, Kambiz Behzadi et al.
U.S. Appl. No. 15/716,533, filed Sep. 27, 2017, Kambiz Behzadi.
U.S. Appl. No. 16/030,603, filed Jul. 9, 2018, Kambiz Behzadi.
U.S. Appl. No. 16/030,824, filed Jul. 9, 2018, Kambiz Behzadi.
U.S. Appl. No. 16/154,033, filed Oct. 8, 2018, Kambiz Behzadi et al.

* cited by examiner

ASSEMBLER FOR MODULAR PROSTHESIS

CROSS REFERENCE TO RELATED APPLICATIONS

This application in a continuation-in-part of U.S. patent application Ser. No. 15/202,434, filed 5 Jul. 2016 that in turn claims benefit of U.S. Patent Application No. 62/277,294, both of which are hereby expressly incorporated by reference in their entireties for all purposes.

FIELD OF THE INVENTION

The present invention relates generally to installation of a prosthesis, and more specifically, but not exclusively, to improvements in prosthesis placement and positioning.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Earlier patents issued to the present applicant have described problems associated with prosthesis installation, for example acetabular cup placement in total hip replacement surgery. See U.S. Pat. Nos. 9,168,154 and 9,220,612, which are hereby expressly incorporated by reference thereto in their entireties for all purposes. Even though hip replacement surgery has been one of the most successful operations, it continues to be plagued with a problem of inconsistent acetabular cup placement. Cup mal-positioning is the single greatest cause of hip instability, a major factor in polyethylene wear, osteolysis, impingement, component loosening and the need for hip revision surgery.

These incorporated patents explain that the process of cup implantation with a mallet is highly unreliable and a significant cause of this inconsistency. The patents note two specific problems associated with the use of the mallet. First is the fact that the surgeon is unable to consistently hit on the center point of the impaction plate, which causes undesirable torques and moment arms, leading to mal-alignment of the cup. Second, is the fact that the amount of force utilized in this process is non-standardized.

In these patents there is presented a new apparatus and method of cup insertion which uses an oscillatory motion to insert the prosthesis. Prototypes have been developed and continue to be refined, and illustrate that vibratory force may allow insertion of the prosthesis with less force, as well, in some embodiments, of allowing simultaneous positioning and alignment of the implant.

There are other ways of breaking down of the large undesirable, torque-producing forces associated with the discrete blows of the mallet into a series of smaller, axially aligned controlled taps, which may achieve the same result incrementally, and in a stepwise fashion to those set forth in the incorporated patents, (with regard to, for example, cup insertion without unintended divergence).

There are two problems that may be considered independently, though some solutions may address both in a single solution. These problems include i) undesirable and unpredictable torques and moment arms that are related to the primitive method currently used by surgeons, which involves manually banging the mallet on an impaction plate mated to the prosthesis and ii) non-standardized and essentially uncontrolled and unquantized amounts of force utilized in these processes.

What is needed is a system and method for improving installation of a prosthesis.

BRIEF SUMMARY OF THE INVENTION

Disclosed is a system and method for improving installation of a prosthesis. The following summary of the invention is provided to facilitate an understanding of some of the technical features related to prosthesis assembly and installation, and is not intended to be a full description of the present invention. A full appreciation of the various aspects of the invention can be gained by taking the entire specification, claims, drawings, and abstract as a whole. The present invention is applicable to other prosthesis in addition to acetabular cups, other modular prosthesis in addition to assembly of modular femoral and humeral prosthesis, and to other alignment and navigation systems in addition to referenced light guides.

An embodiment of the present invention may include axial alignment of force transference, such as, for example, an axially sliding hammer moving between stops to impart a non-torqueing installation force. There are various ways of motivating and controlling the sliding hammer, including a magnitude of transferred force. Optional enhancements may include pressure and/or sound sensors for gauging when a desired depth of implantation has occurred.

Other embodiments include adaptation of various devices for accurate assembly of modular prostheses, such as those that include a head accurately impacted onto a trunnion taper that is part of a stem or other element of the prosthesis.

Still other embodiments include an alignment system to improve site preparation, such as, for example, including a projected visual reference of a desired orientation of a tool and then having that reference marked and available for use during operation of the tool to ensure that the alignment remains proper throughout its use, such as during a reaming operation.

Further embodiments include enhancement of various tools, such as those used for cutting, trimming, drilling, and the like, with ultrasonic enhancement to make the device a better cutting, trimming, drilling, etc. device to enable its use with less strength and with improved accuracy.

An embodiment of the present invention may include a grip structure on a body of modular assembly that may provide an anchor for defining an alignment axis for a trunnion of the body and a head to be installed onto the trunnion.

An embodiment of the present invention may include a head grasper that secures the head into an optimized assembly position relative to the alignment axis/trunnion. The optimized assembly position may include non-relative canting and alignment with the alignment axis.

An embodiment of the present invention may include a holder that engages a grip structure and is coupled to a head grasper. The holder may aid in reducing waste of energy used in assembly of the head onto the trunnion and it may aid in the optimized positioning of the head relative to the alignment axis/trunnion before and/or during installation of the head onto the trunnion.

An embodiment of the present invention may include use of force source coupled to a head grasper/tool to generate assembly forces to install the head onto the trunnion. The force source may deliver one or more of a dynamic assembly force, a vibratory assembly force, a set of discrete assembly impacts, other assembly forces, and combinations thereof. The assembly force(s) may be applied the head grasper/tool to install the head onto the trunnion. The assembly force(s) may be constrained to operate along the alignment axis, and may be reduced by securing/anchoring the body of the modular prosthesis, such as by using a grip structure.

An embodiment of the present invention may include use of a force sensing mechanism coupled to a head grasper/tool to measure, possibly in true realtime (e.g., during dynamic operation of the tool to apply the assembly force(s)), the assembly force(s).

An embodiment of the present invention may include development and production of standards, guidelines, recommendations for an optimum force, or force range for the assembly force(s) to achieve a desired cold weld.

A modular prosthesis body, including a stem portion; a trunnion portion coupled to the stem portion, the trunnion portion having an insertion profile defining an insertion axis; and a grip structure coupled to the trunnion portion and disposed on the insertion axis.

A system for assembly of a modular prosthesis including a stem portion, a trunnion portion coupled to the stem portion, the trunnion portion having an insertion profile defining an insertion axis, and a prosthesis head configured to be installed on the trunnion portion and defining an installation aperture complementary to the insertion profile with the installation aperture defining an installation axis, including a head grasper including a housing defining a cavity complementary to an outer portion of the prosthesis head with the housing having a grasper axis extending through the cavity wherein the housing is configured to secure the prosthesis head within the cavity and align the grasper axis with the installation axis.

A method, including a) installing a set of prosthetic heads onto a set of associated trunnions to produce a set of cold welds using a range of measured assembly forces; and b) establishing, responsive to the range of measured assembly forces, a set of ranges of optimized assembly forces to predict production of a cold weld for a particular one prosthetic head installed onto a particular associated trunnion.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1 illustrates an embodiment of the present invention for a sliding impact device;

FIG. 2 illustrates a lengthwise cross-section of the embodiment illustrated in FIG. 1 including an attachment of a navigation device;

FIG. 3 illustrates a cockup mechanical gun embodiment, an alternative embodiment to the sliding impact device illustrated in FIG. 1 and FIG. 2;

FIG. 4 illustrates an alternative embodiment to the devices of FIG. 1-3 including a robotic structure;

FIG. 5 illustrates an alternative embodiment to the devices of FIG. 1-4 including a pressure sensor to provide feedback;

FIG. 6 illustrates an alternative embodiment to the feedback system of FIG. 5 including a sound sensor to provide feedback for the embodiments of FIG. 1-5;

FIG. 7 illustrates a modular prosthesis and assembly tools;

FIG. 8 illustrates a femoral head to be assembled onto a trunnion attached to a femoral stem;

FIG. 9 illustrates alignment of an installation device with the femoral head for properly aligned impaction onto the trunnion, such as an embodiment of FIG. 1-FIG. 6 adapted for this application;

FIG. 10 illustrates use of a modified vibratory system for assembly of the modular prosthesis;

FIG. 11 illustrates an environment in which a prosthesis is installed highlighting problem with site preparation;

FIG. 12 illustrates an alignment system for preparation and installation of a prosthesis;

DETAILED DESCRIPTION OF THE INVENTION

Figure 1:
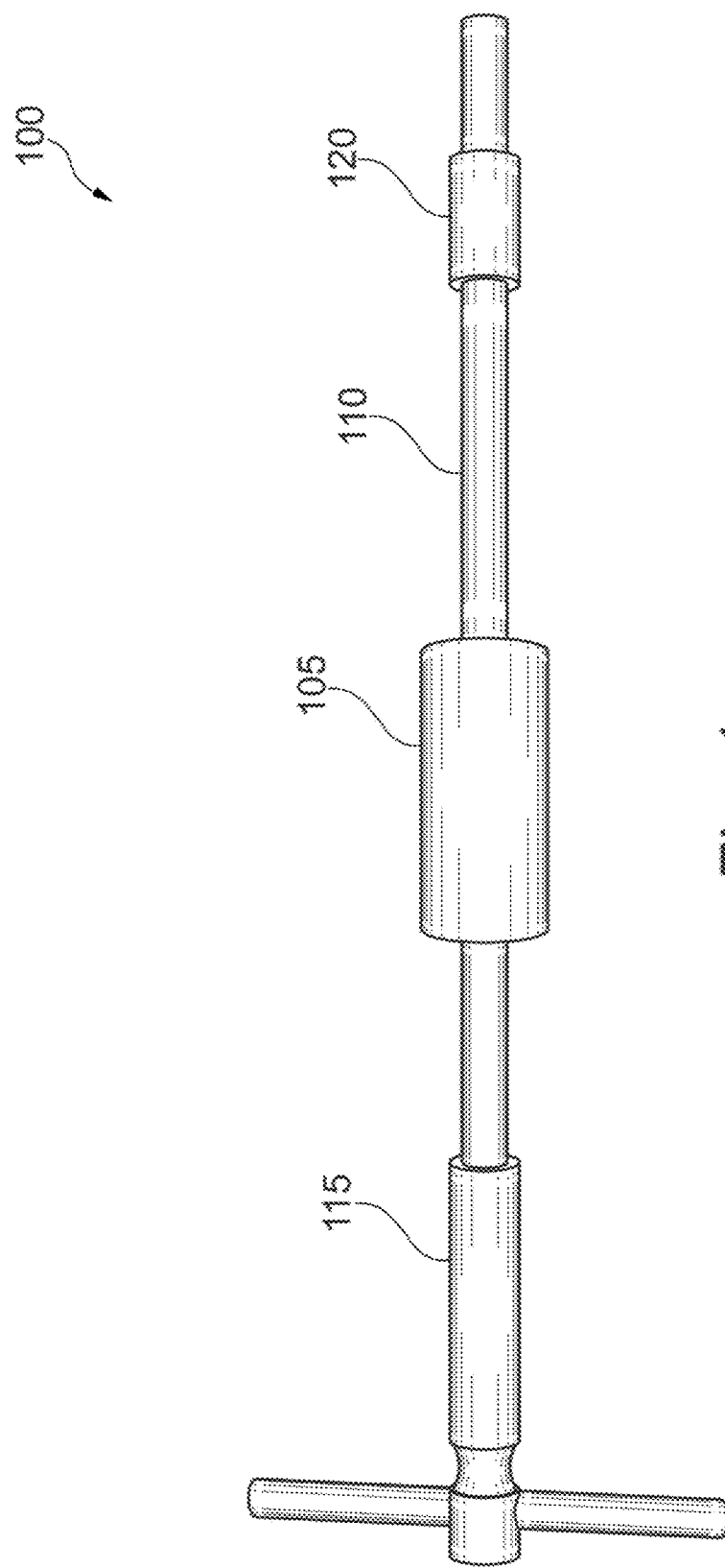
FIG. 1-FIG. 6 illustrate embodiments including installation of a prosthesis, including installation into living bone.

Embodiments of the present invention provide a system and method for improving installation of a prosthesis. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

Embodiments of the present invention may include one of more solutions to the above problems. The incorporated U.S. Pat. No. 9,168,154 includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a structure (e.g., hollow cylindrical mass) that travels over a stainless rod.

Figure 2:
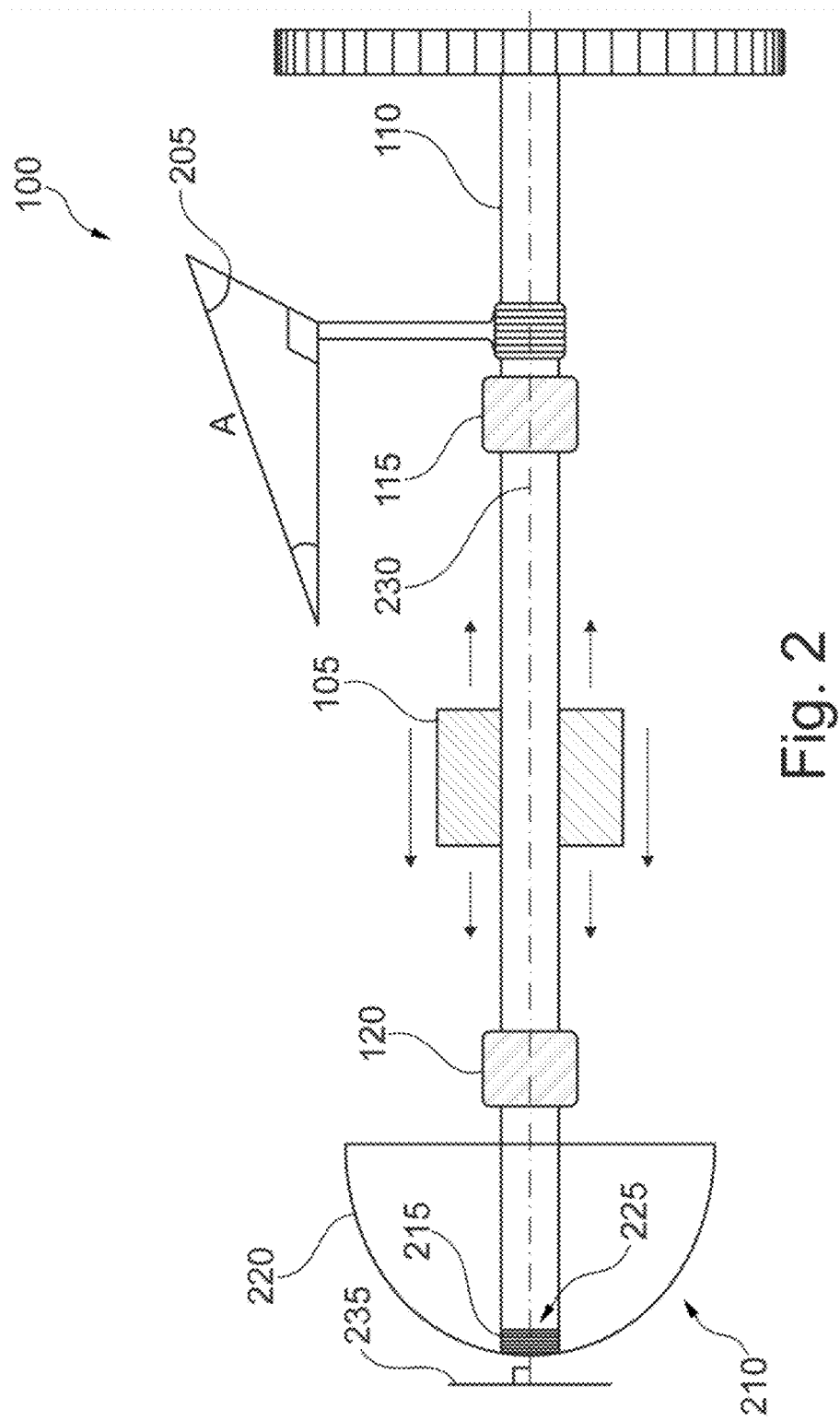

FIG. 1 illustrates an embodiment of the present invention for a sliding impact device 100, and FIG. 2 illustrates a lengthwise cross-section of sliding impact device 100 including an attachment of a navigation device 205.

Device 100 includes a movable hammer 105 sliding axially and freely along a rod 110. Rod 110 includes a proximal stop 115 and distal stop 120. These stops that may be integrated into rod 110 to allow transference of force to rod 110 when hammer 105 strikes distal stop 120. At a distal end 210 of rod 110, device 100 includes an attachment system 215 for a prosthesis 220. For example, when prosthesis 220 includes an acetabular cup having a threaded cavity 225, attachment system 215 may include a complementary threaded structure that screws into threaded cavity 225. The illustrated design of device 100 allows only a perfect axial force to be imparted. The surgeon cannot deliver a blow to the edge of an impaction plate. Therefore the design of this instrument is in and of itself protective, eliminating a problem of "surgeon's mallet hitting on the edge of the impaction plate" or other mis-aligned force transference, and creating undesirable torques, and hence unintentional mal-alignment of prosthesis 220 from an intended position/orientation.

A longitudinal axis 230 extends through the ends of rod 110. Attachment system 215 aligns prosthesis 220 to axis 230 when rod 110 is coupled to threaded cavity 225. An apex of prosthesis 220 (when it generally defines a hollow semi-spherical shell) supports a structure that defines threaded cavity 225 and that structure may define a plane 235 that may be tangent to the apex, with plane 235 about perpendicular to axis 230 when rod 110 engages prosthesis 220. Operation of device 100 is designed to deliver only axial (e.g., aligned with axis 230 and thus non-torqueing) forces to prosthesis 220. Other embodiments illustrated in FIG. 3-FIG. 6 may be similarly configured.

Figure 3:
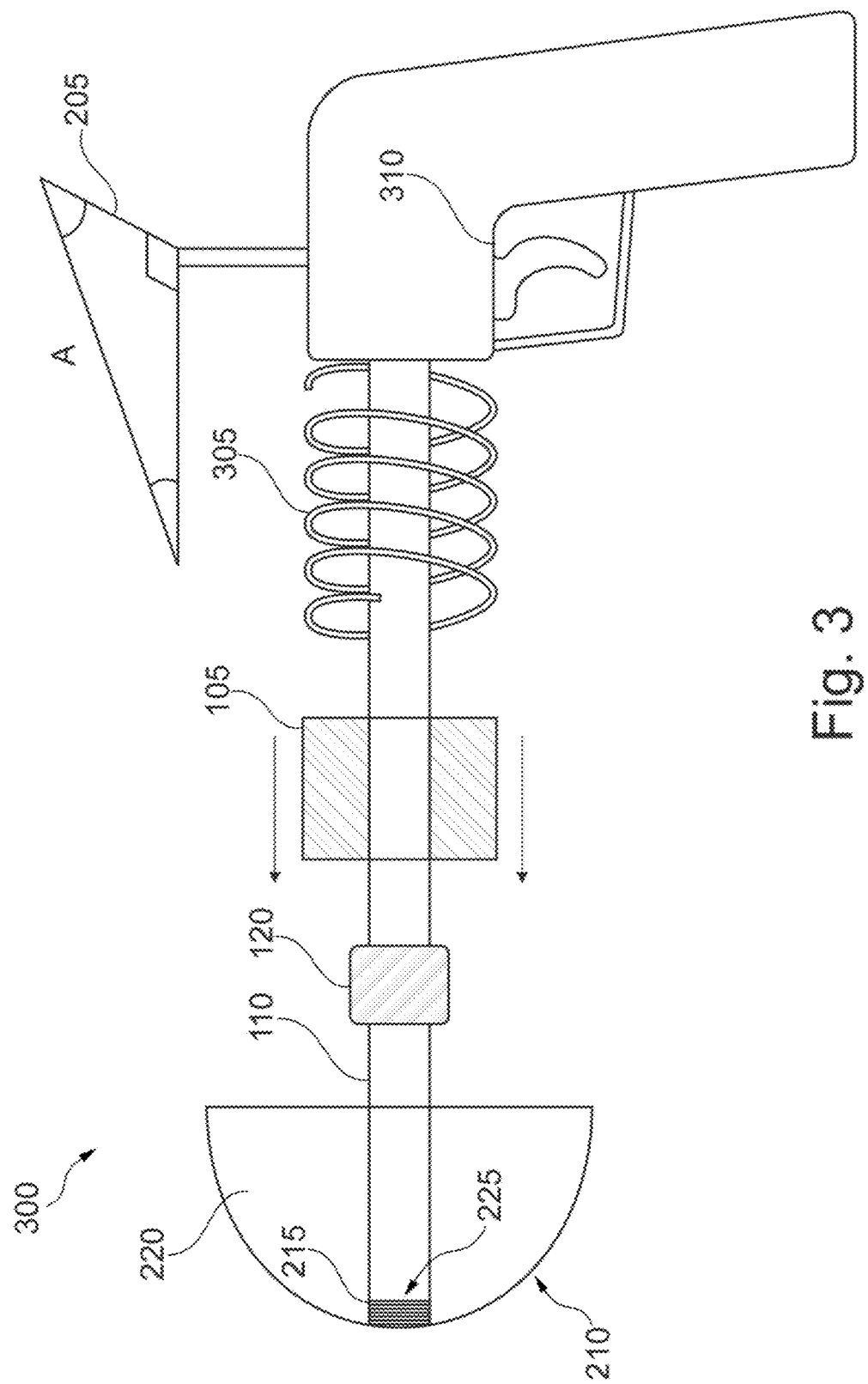

FIG. 3 illustrates a cockup mechanical gun 300 embodiment, an alternative embodiment to the sliding impact device illustrated in FIG. 1 and FIG. 2. An alternate embodiment includes cockup mechanical gun 300 that uses the potential energy of a cocked up spring 305 to create an axially aligned impaction force. Hammer 105 is drawn back and spring 305 is locked until an operator actuates a trigger 310 to release spring 305 and drive hammer 105 along rod 110 to strike distal stop 120 and transfer an axially aligned impacting force to prosthesis 220.

Each pull of trigger 310 creates the same predetermined fixed unit of force (some alternatives may provide a variably predetermined force). The surgeon cannot deliver a mis-aligning impact to an impaction plate with this design.

Figure 4:
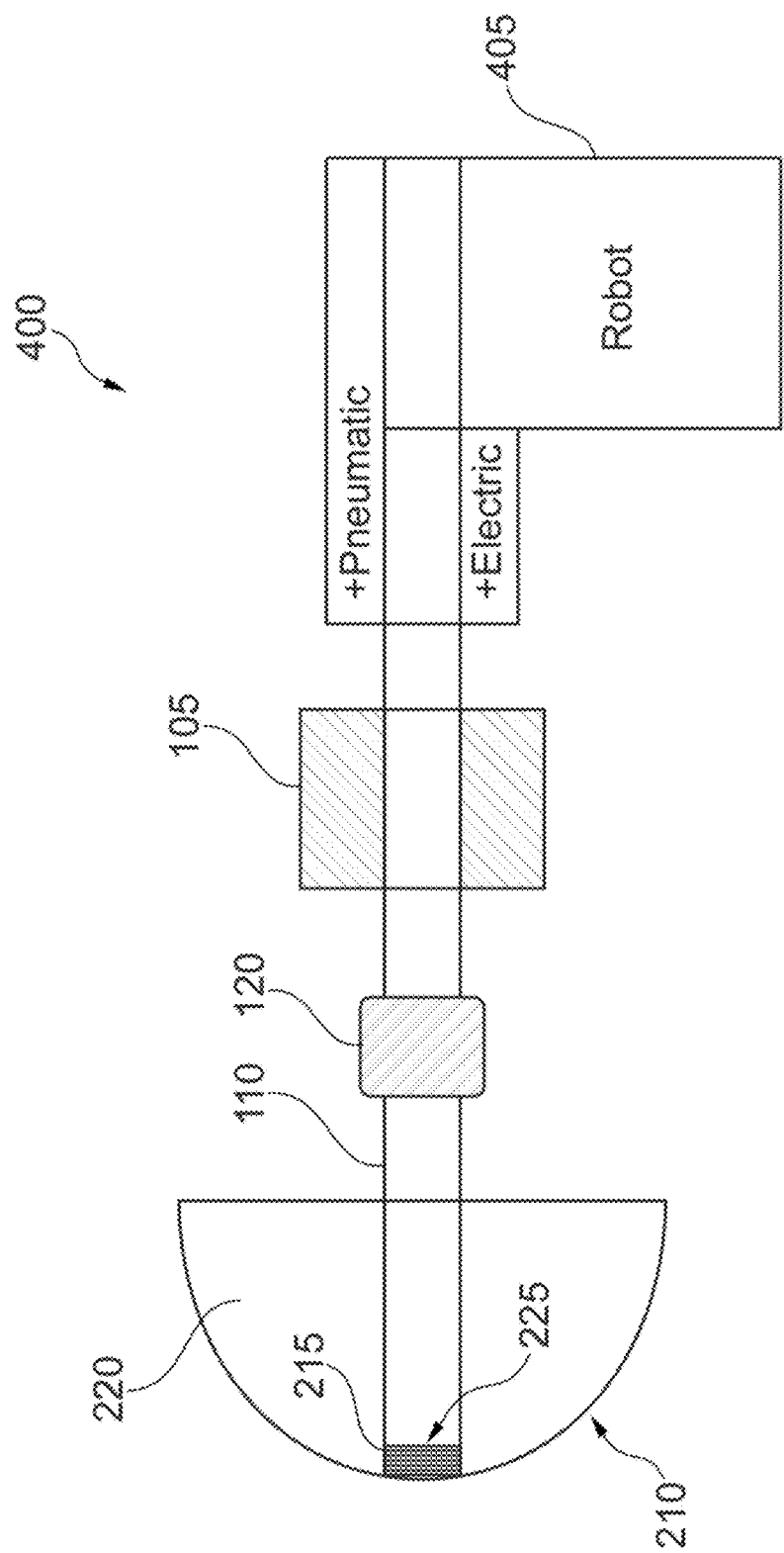

FIG. 4 illustrates an alternative robotic device 400 embodiment to the devices of FIG. 1-3 including a robotic control structure 405. For example, device 100 and/or device 300 may be mounted with robot control structure 405 and the co-axial impacts may be delivered mechanically by a robotic tool using pneumatic or electric energy.

Figure 5:
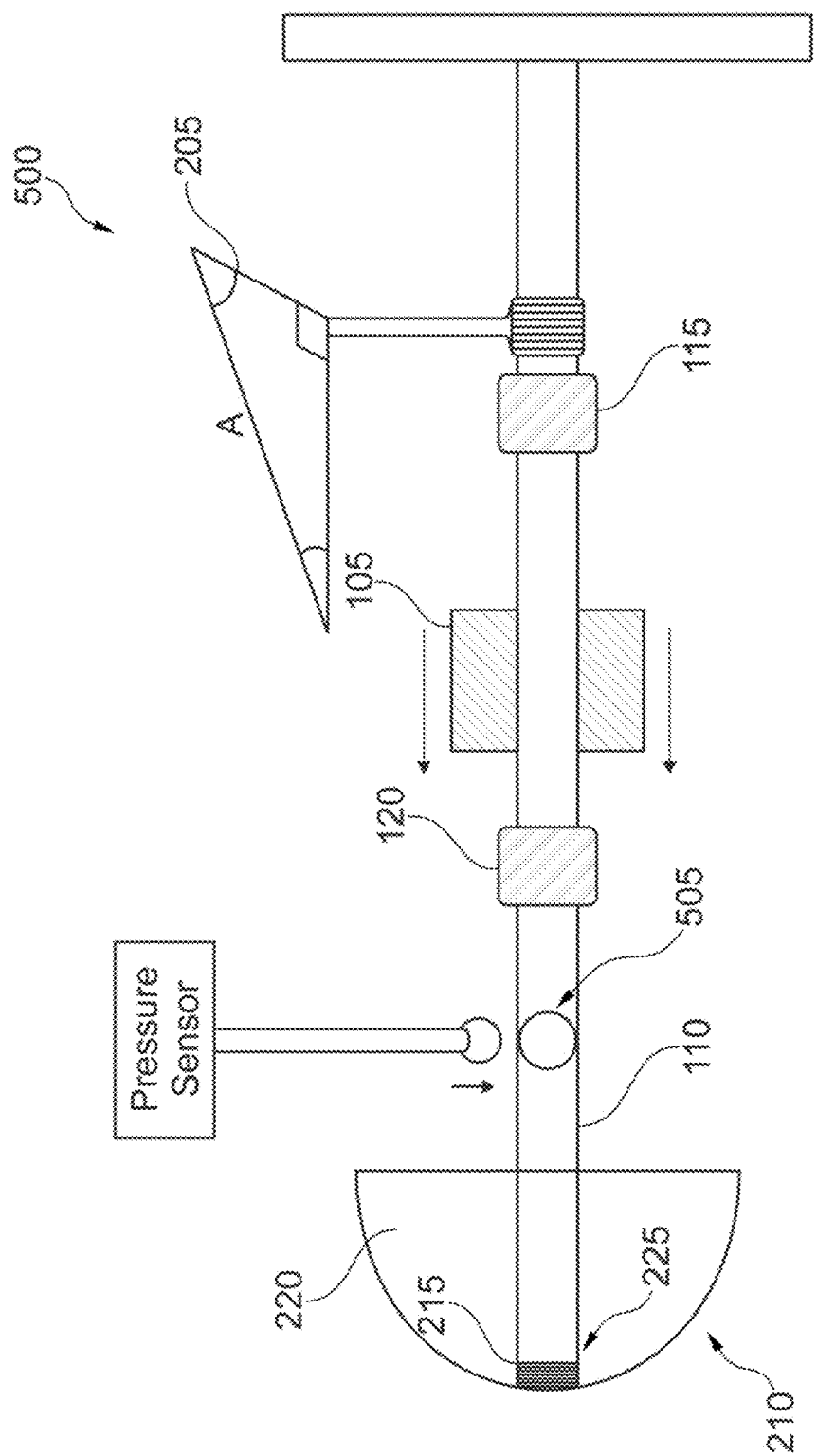

FIG. 5 illustrates an alternative embodiment 500 to the devices of FIG. 1-4 including a pressure sensor 505 to provide feedback during installation. With respect to management of the force required for some of these tasks, it is noted that with current techniques (the use of the mallet) the surgeon has no indication of how much force is being imparted onto the implant and/or the implant site (e.g., the pelvis). Laboratory tests may be done to estimate what range of force should be utilized in certain age groups (as a rough guide) and then fashioning a device 500, for example a modified sledgehammer 100 or cockup gun 300 to produce just the right amount of force. Typically the surgeon may use up to 2000 N to 3000 N of force to impact a cup into the acetabular cavity. Also, since some embodiments cannot deliver the force in an incremental fashion as described in association with the BMD3 device, device 500 includes a stopgap mechanism. Some embodiments of the BMD3 device have already described the application of a sensor in the body of the impaction rod. Device 500 includes sensing system/assembly 505 embedded in device 500, for example proximate rod 110 near distal end 210, and used to provide valuable feedback information to the surgeon. Pressure sensor 505 can let the surgeon know when the pressures seems to have maximized, whether used for the insertion of an acetabular cup, or any other implant including knee and shoulder implants and rods used to fix tibia and femur fractures. When pressure sensor 505 is not showing an advance or increase in pressure readings and has plateaued, the surgeon may determine it is time to stop operation/impacting. An indicator, for example an alarm can go off or a red signal can show when maximal peak forces are repeatedly achieved. As noted above, the incorporated patents describe a presence of a pressure sensor in an installation device, the presence of which was designed as part of a system to characterize an installation pulse pattern communicated by a pulse transfer assembly. The disclosure here relates to a pressure sensor provided not to characterize the installation pulse pattern but to provide an in situ feedback mechanism to the surgeon as to a status of the installation, such as to reduce a risk of fracturing the installation site. Some embodiments may also employ this pressure sensor for multiple purposes including characterization of an applied pulse pattern such as, for example, when the device includes automated control of an impacting engine coupled to the hammer. Other embodiments of this invention may dispose the sensor or sensor reading system within a handle or housing of the device rather than in the central rod or shaft.

Figure 6:
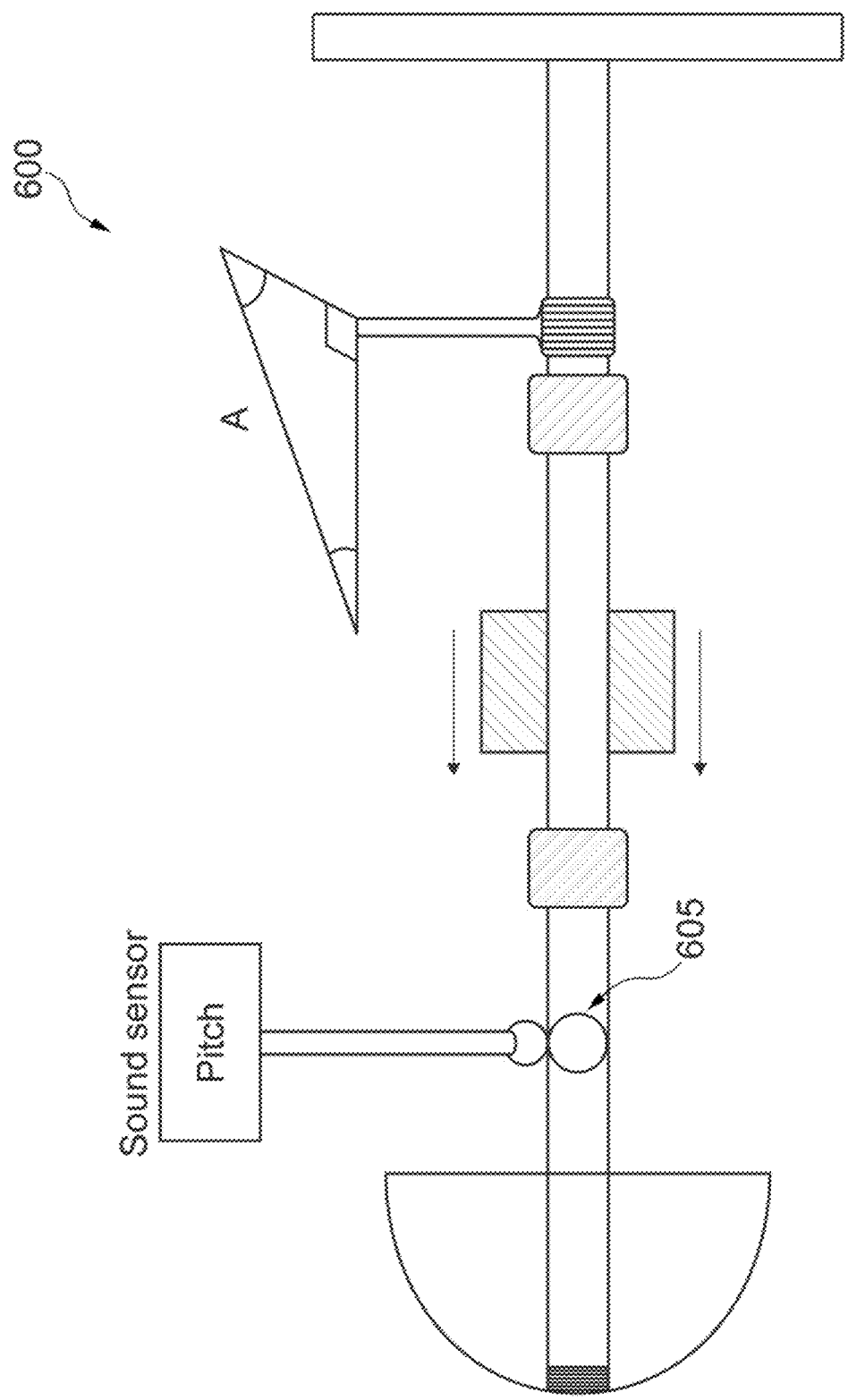

FIG. 6 illustrates an alternative device 600 embodiment to the feedback system of FIG. 5 including a sound sensor 605 to provide feedback for the embodiments of FIG. 1-5. Surgeons frequently use a change in pitch (sound) to gauge whether an implant (e.g., the cup) has "bottomed out" (an evaluation of a "seatedness" of the implant) and device 600 includes sound sensor 605 either attached or coupled to rod 110 or otherwise disposed separately in the operating room. Sound sensor system/assembly 605 may be used in lieu of, or in addition to, pressure sensor system/assembly 505 illustrated in FIG. 5.

Figure 7:
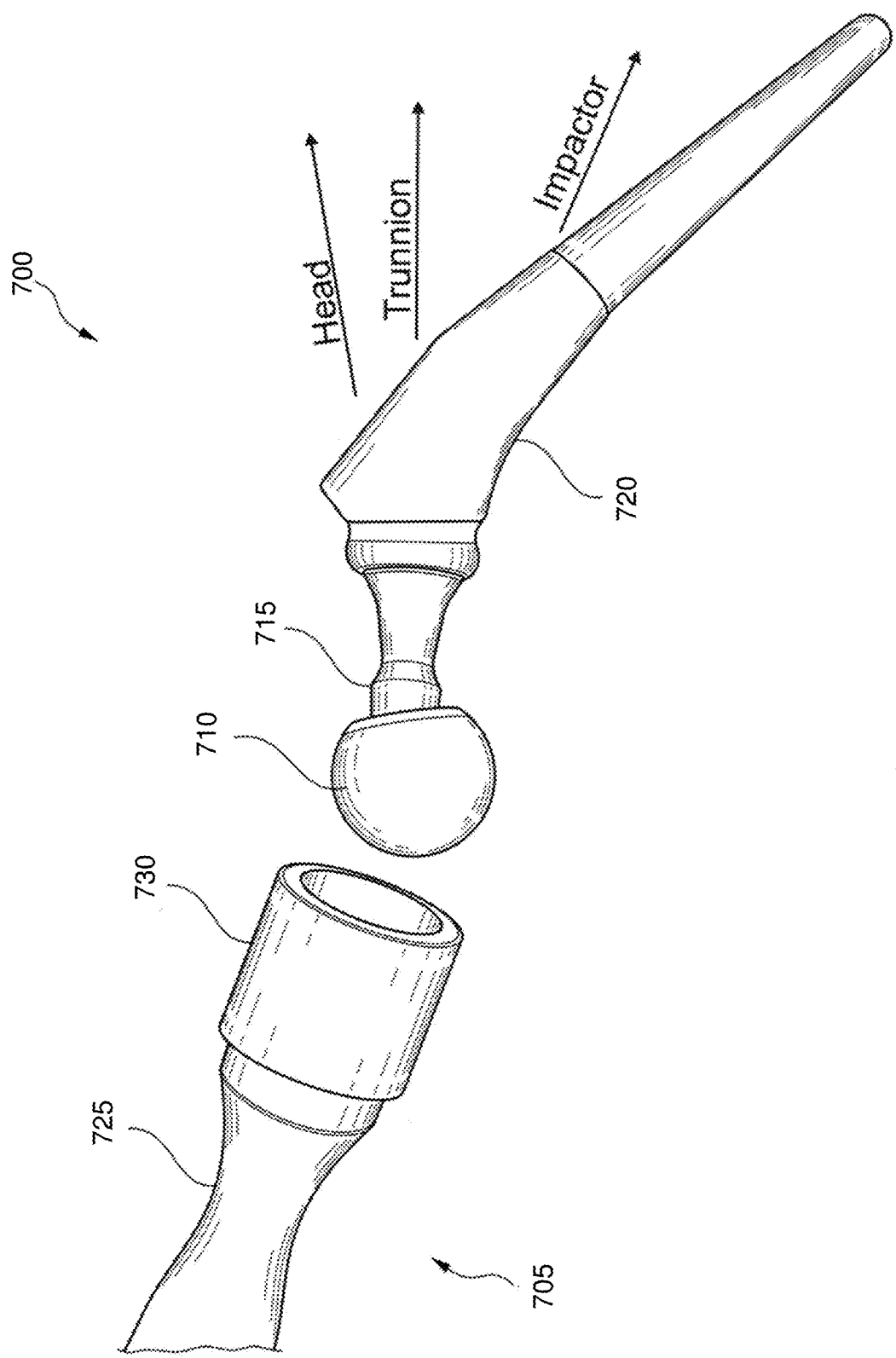
FIG. 7-FIG. 10 illustrate prosthesis assembly embodiments including use of variations of the prosthesis installation embodiments of FIG. 1-FIG. 6, such as may be used to reduce a risk of trunnionosis.

FIG. 7-FIG. 10 illustrate prosthesis assembly embodiments including use of variations of the prosthesis installation embodiments of FIG. 1-FIG. 6, such as may be used to reduce a risk of trunnionosis or for other advantage. FIG. 7 illustrates a modular prosthesis 700 and assembly tool 705. Prosthesis 700 includes a head 710 and a trunnion taper 715 at an end of a stem 720 (e.g., a femoral stem for supporting a ball head to fit within an acetabular cup used in a total hip replacement procedure). During the procedure, the surgeon assembles prosthesis 700 by using tool 705 which may include an impact rod 725 attached to a head coupler 730. The surgeon uses tool 705 to drive head 710 onto trunnion taper 715 which conventionally includes a free mallet striking tool 705. Such a procedure may be prone to the similar problems as installation of a prosthesis into an implant site, namely application of off-axis torqueing forces and an uncertainty of applied force and completion of assembly.

It is believed that even a 0.1 degree mal-alignment on head 710 on trunnion taper 715 may lead to progressive wear and metalosis. Variations of the embodiments of devices illustrated in FIG. 1-FIG. 6 and its associated content may be developed to help resolve this problem. In the case of "non-torqueing axiallity" of forces from an assembly device, a bore of the head may define an axis, the trunnion taper may define an axis, with the assembly device aligning these axes and then applying its forces in co-axial alignment with these co-axially aligned axes. Such an embodiment may reduce or eliminate any force-responsive rotations of the head with respect to the taper as the head is seated into position by the assembly device.

Figure 8:
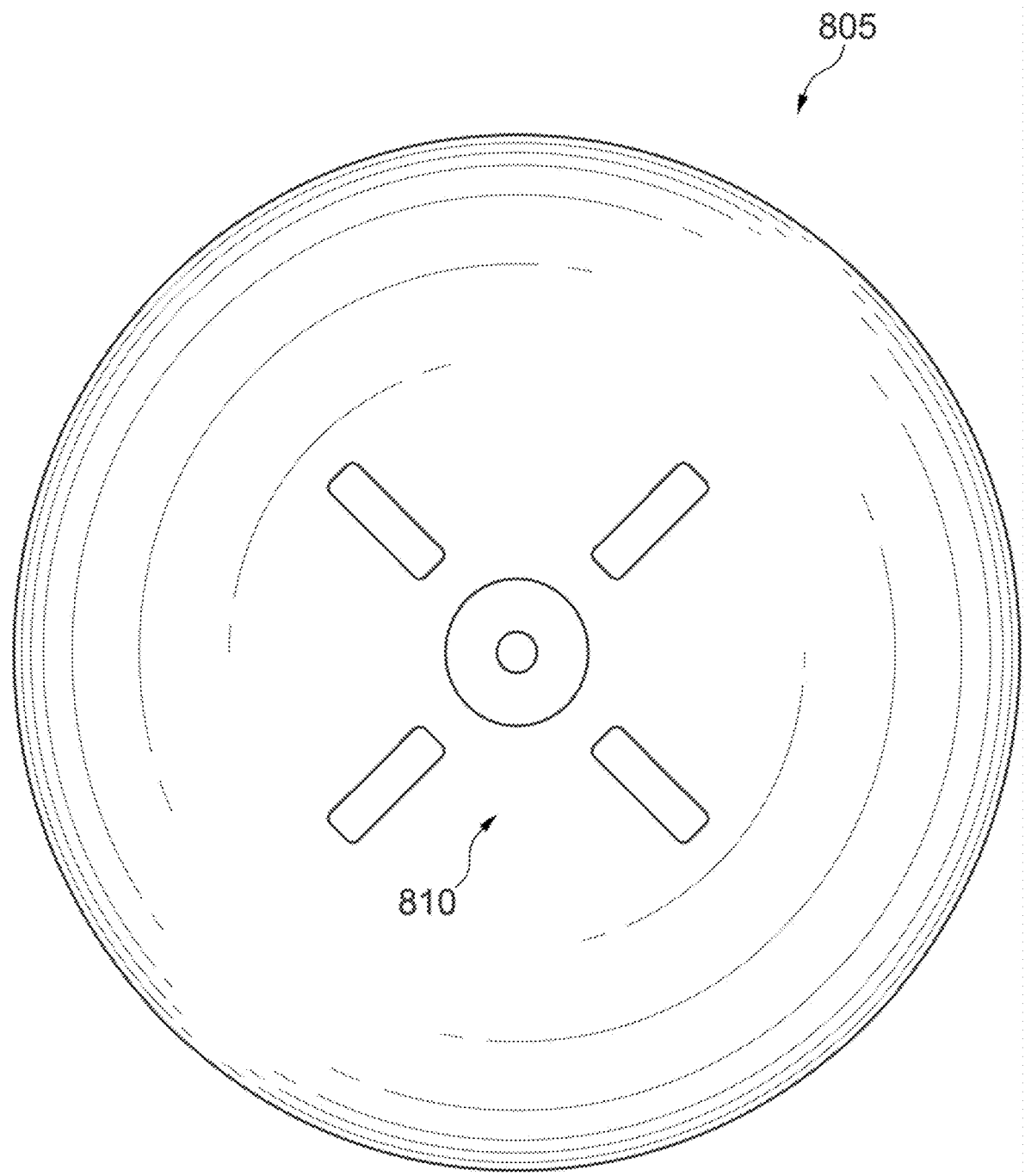

FIG. 8 illustrates a femoral head 805, a variation of head 710 illustrated in FIG. 7, to be assembled onto trunnion taper 715 that is coupled to femoral stem 720. A center dot 810 may be placed on femoral (or humeral) head 805 to be impacted using tool 705.

Figure 9:
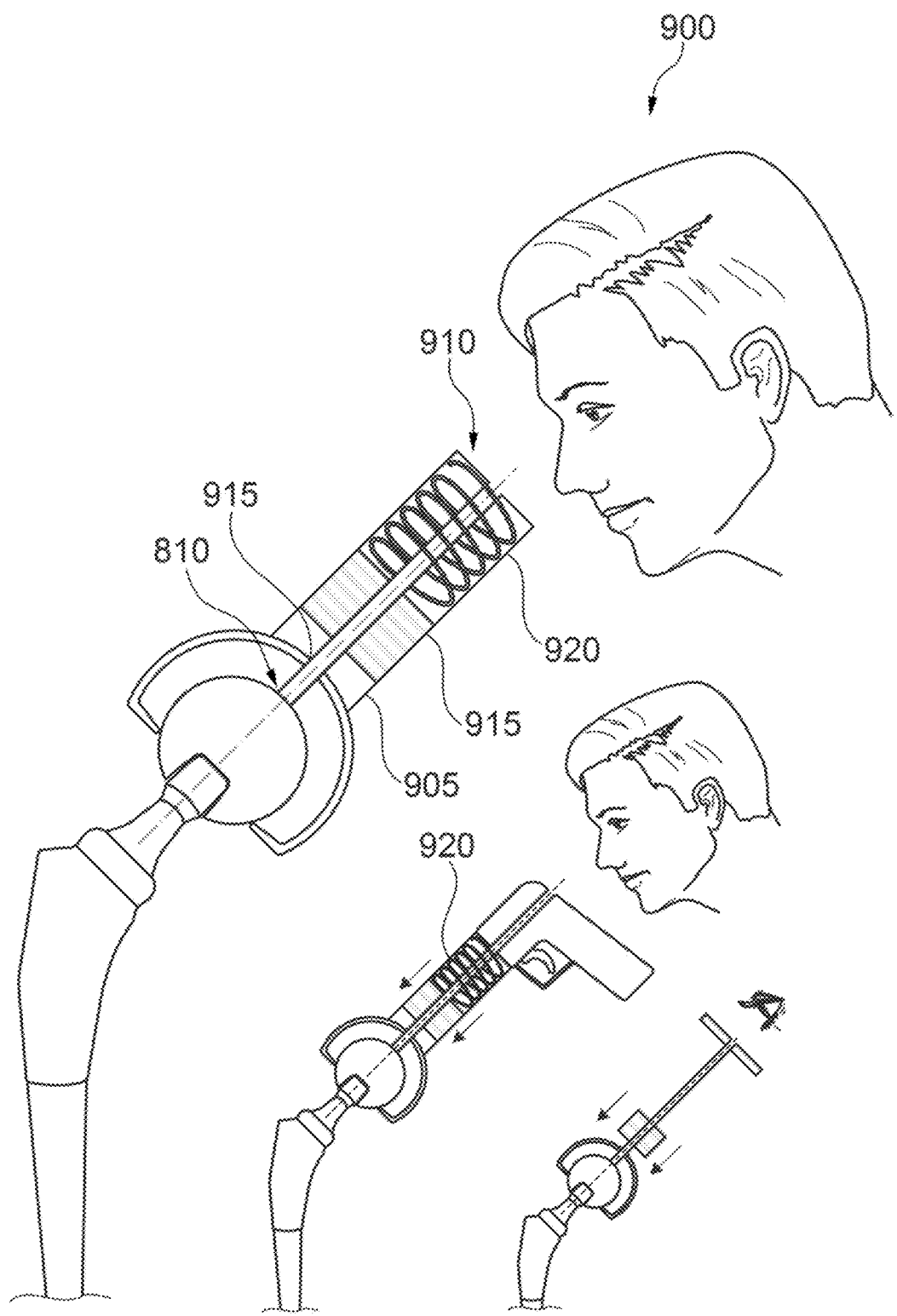

FIG. 9 illustrates alignment of an installation device 900, a variation of any of devices 100-600, with femoral head 805 for properly aligned impaction onto trunnion taper 715, such as an embodiment of FIG. 1-FIG. 6 adapted for this application. Such adaptation may include, for example, an axial channel 910 to view dot 810, and align force transference, prior to operation of hammer 105.

Dot 810 can be aligned with an impactor/device/gun. Once axial alignment, such as through the sight channel, has been confirmed, a sledgehammer, a cockup gun, or other similar device can bang the impactor onto femoral (humeral) head 805 to impact it on trunnion taper 715. The co-axiality of the head and the device can be confirmed visually (for example, through a hollow cylinder that comprises a center shaft of the device) or with a variety of electronic and laser methods.

Figure 10:
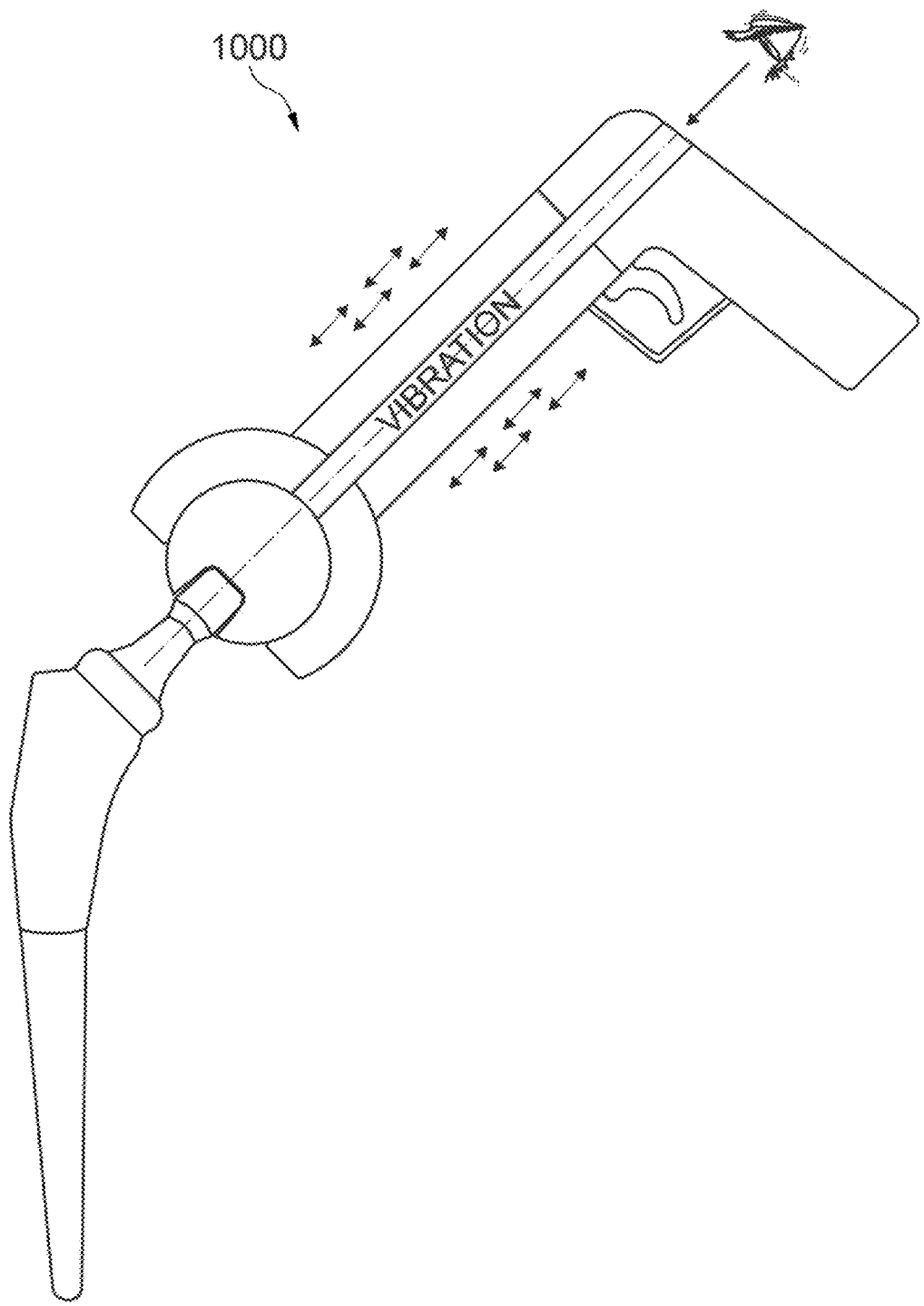

FIG. 10 illustrates use of a modified vibratory system 1000, a variation of installation device 900 for assembly of the modular prosthesis illustrated in FIG. 7. Alternatively to device 900, a variation of the BMD3 device can be used to insert the femoral and humeral heads 710 onto trunnion taper 715. For example, a version of the BMD3 device where femoral head 710 is grasped by a "vibrating gun" and introduced methodically and incrementally onto trunnion taper 715. Since there are no large forces being applied to the head/trunnion junction, there is essentially no possibility, or a reduced possibility, of head 710 seating onto trunnion taper 715 in a misaligned fashion. It would be possible to use the same technique of marking the center of head 710 and lining it up with trunnion taper 715 and device axially before operating the device.

Figure 11:
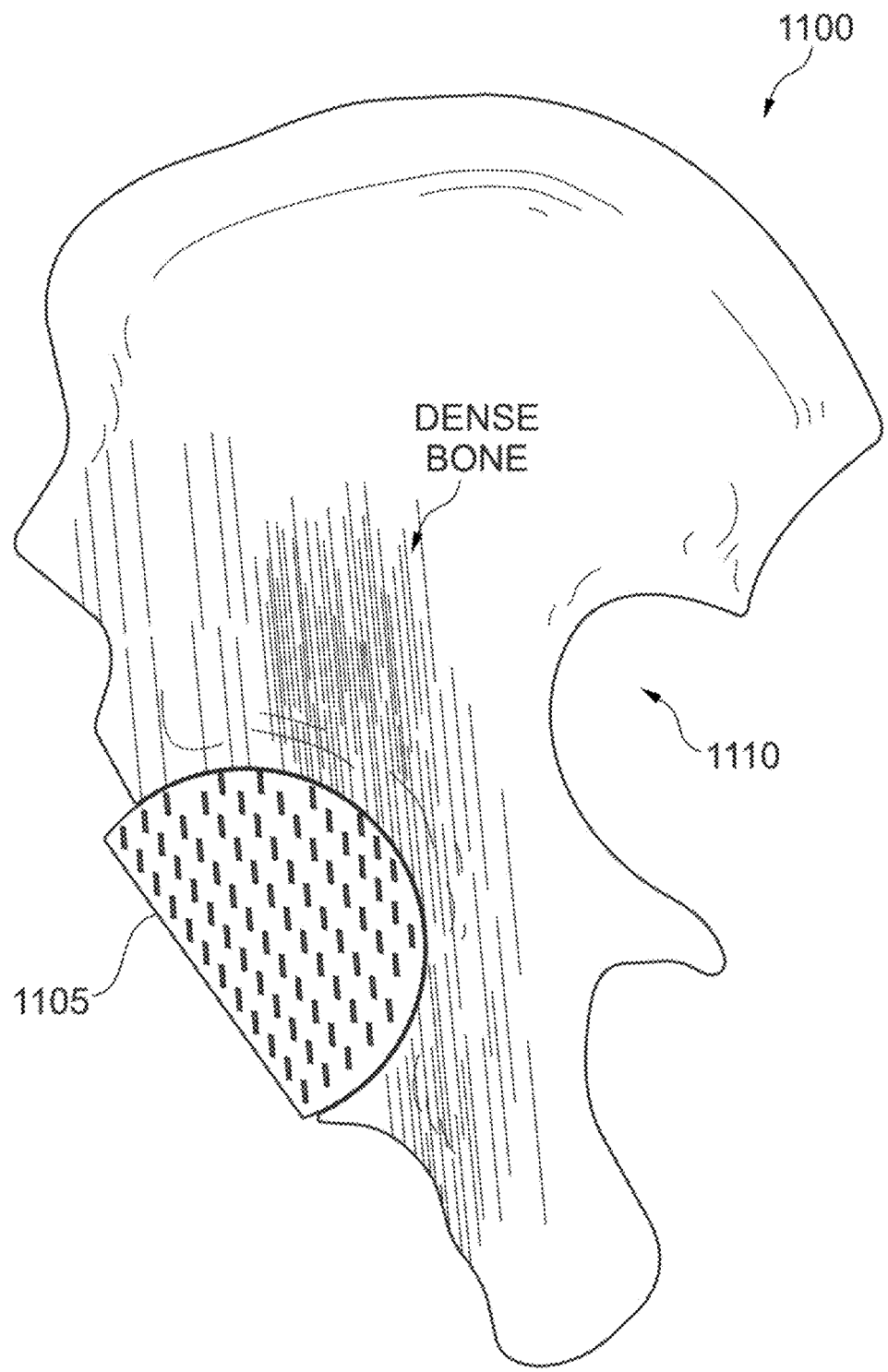
FIG. 11-FIG. 12 illustrate an improvement to site preparation for an installation of a prosthesis.
Figure 12:
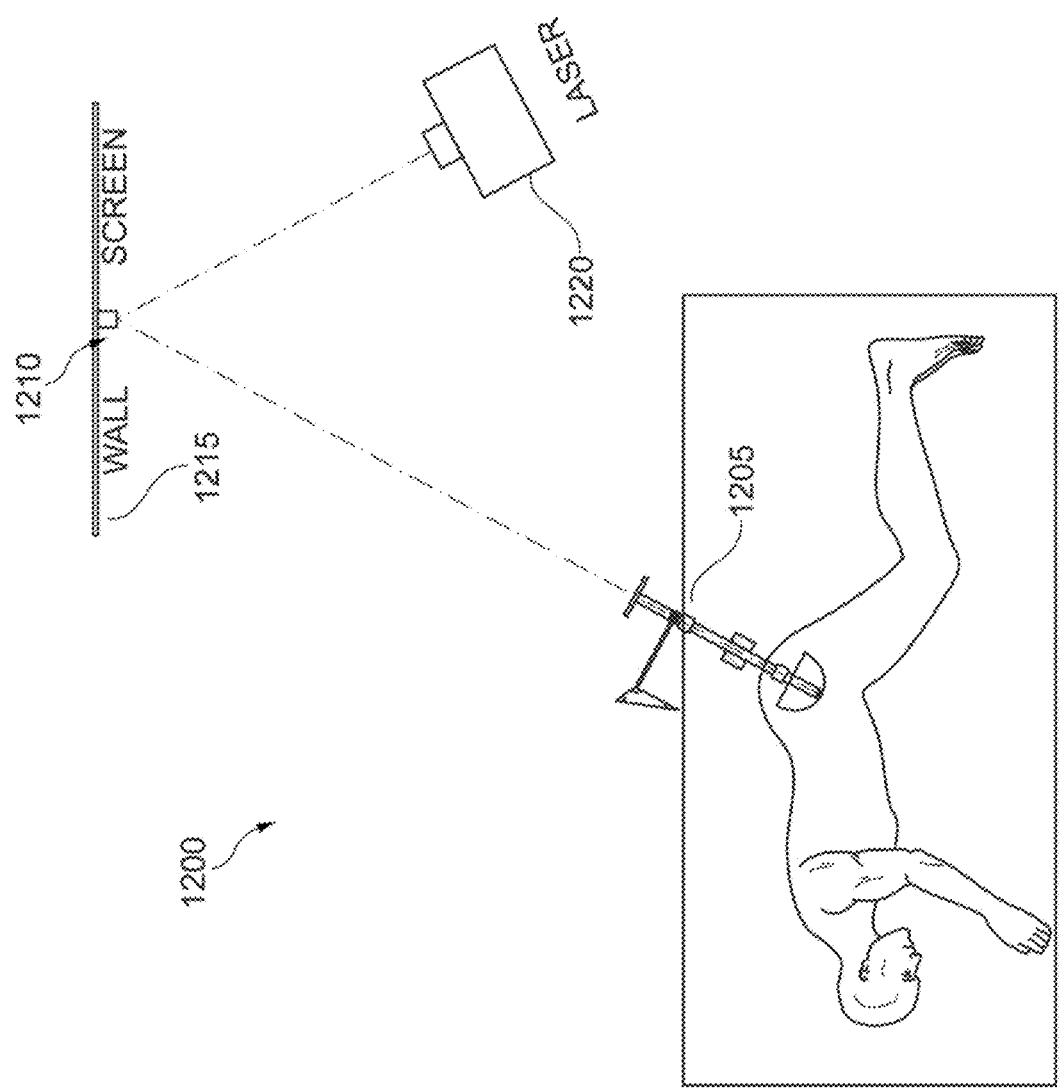

FIG. 11-FIG. 12 illustrate an improvement to site 1100 preparation for an installation of a prosthesis 1105. FIG. 11 illustrates an environment 1100 in which prosthesis 1105 is installed highlighting a problem with site preparation for a prosthesis installation procedure having variable density bone (line thickness/separation distance reflecting variable bone density) of acetabulum 1110.

There is a secondary problem with the process of acetabular preparation and implantation that leads to cup malalignment. Currently, during the process of acetabular reaming, surgeons make several assumptions. One common assumption is that the reamer is fully seated in a cavity and surrounded on all sides by bone. Another common assumption is that the bone that is being reamed is uniform in density. Imagine a carpenter that is preparing to cut a piece of wood with a saw. Now imagine that parts of this piece of wood are embedded with cement and some parts of the piece of wood are hollow and filled with air. The carpenter's saw will not produce a precise cut on this object. Some parts are easy to cut and some parts are harder to cut. The saw blades skives and bends in undesirable ways. A similar phenomenon happens in acetabular preparation with a reamer and when performing the cuts for knee replacement with a saw. With respect to the acetabulum, the side of the cavity that is incomplete (side of the reamer that is uncovered) will offer less resistance to the reamer and therefore the reamer preferentially reams towards the direction of the uncovering. Second, the reamer cuts the soft bone much more easily than the dense and sclerotic bone, so the reamer moves away from the sclerotic bone and moves toward the soft bone. From a machining perspective, the reaming and preparation of the acetabulum may not be concentric or precise. This maybe a significant factor in the surgeon's inability to impact the cup in the desired location FIG. 12 illustrates an alignment system 1200 for preparation and installation of a prosthesis to help address/minimize this effect. A first step that can be taken is to include directionality into the process of reaming at the outset, and not just at the last step during impaction. Current technique allows the surgeon to ream the cup haphazardly moving the reamer handle in all directions, being ignorantly unaware that he is actually creating a preference for the sinking path of the acetabular implant. Ultimately the direction in which the surgeon reams may in fact be determining the position/path of the final implant. The surgeon then impacts the cup using the traditional A-frame or any of the currently used intra-operative measurement techniques such as navigation or fluoroscopy. These methods provide information about the position of the cup either as it is being implanted or after the implantation has occurred. None of these techniques predetermine the cup's path or function to guide the cup in the correct path.

Proposed is a method and a technique to eliminate/reduce this problem. Before the surgeon begins to ream the acetabulum, the reamer handle should be held, with an A-frame attached, in such a way to contemplate the final position of the reamer and hence the implant, (e.g., hold the reamer in 40 degree abduction and 20 degree anteversion reaming is started). This step could also be accomplished with navigation or fluoroscopy. The surgeon could, for example, immediately mark this position on a screen or the wall in the operating room as described below and as illustrated in FIG. 12. After the anticipated position of the reamer is marked, the surgeon can do whatever aspect of reaming that needs to be done. For example the first reaming usually requires medialization in which the reamer is directed quite vertically to ream in to the pulvinar. Typically three or four reamings are done. First, the acetabular cavity is medialized. The other reamings function to get to the subchondral bone in the periphery of the acetabulum. One solution may be that after each reaming, the reamer handle be held in the final anticipated position of the implant. In some cases it may be difficult to have an A-frame attached to every reamer and to estimate the same position of the reamer in the operating space accurately with the A-frame.

An alternative to that is also proposed to address this process. For example, at a proximal end of the reamer shaft handle will be placed a first reference system 1205, for example a laser pointer. This laser pointer 1205 will project a spot 1210 either on a wall or on a screen 1215, a known distance from the operating room table. That spot 1210 on wall 1215 (or on the screen) is then marked with another reference system 1220, for example a second independent laser pointer that sits on a steady stand in the operating room. Thereafter manipulating the shaft handle so that the first reference system has the desired relationship, example co-aligned, with the second reference system, the surgeon knows that the device attached to the handle has the desired orientation. So when the first reamer is held in the anticipated and desired final alignment of the implant (e.g., 40 degree abduction, 20 degree anteversion for many preferred installation angles of an acetabular cup), the laser pointer at the proximal end of the reamer handle projects a spot on the wall or screen. That spot is marked with the second stationary laser, and held for the duration of the case. All subsequent reamings will therefore not require an A-frame to get a sense of the proper alignment and direction of the reamer. The surgeon assures that no matter how he moves the reamer handle in the process of reaming of the acetabulum, that the reaming finishes with the reamer handle (laser pointer) pointing to the spot on the wall/screen. In this manner, directionality is assured during the reaming process. In this way the sinking path of the actual implant is somewhat predetermined. And no matter what final intra-operative monitoring technique is used (A-frame, C-Arm, Navigation) that the cup will likely seat/sink more closely to the desired final position.

Figure 13:
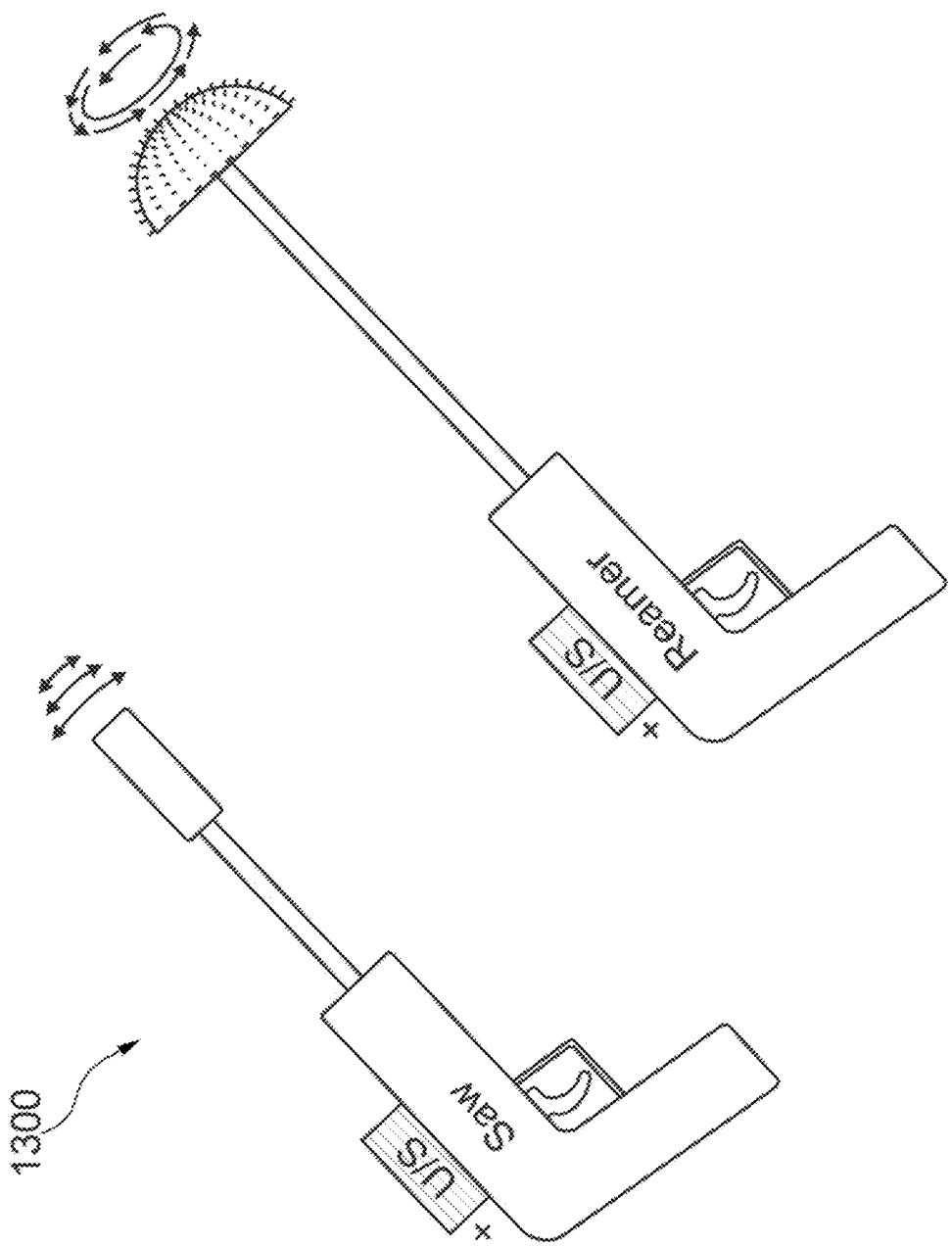
FIG. 13 illustrates modified surgical devices incorporating vibratory energy as at least an aid to mechanical preparation.

FIG. 13 illustrates modified surgical devices 1300 incorporating vibratory energy as at least an aid to mechanical preparation. Also proposed herein is another concept to address a problem associated with non-concentric reaming of the acetabulum caused by variable densities of the bone and the uncovering of the reamer. Imagine the same carpenter has to cut through a construct that is made out of wood, air, and cement. The carpenter does not know anything about the variable densities of this construct. There are two different saws available: one that cuts effectively through wood only, and ineffectively through the cement. Also available is a second saw that cuts just as effectively through cement as wood. Which of these saws would improve a chance of producing a more precise cut? Proposed is a mixing of ultrasonic energy with the standard oscillating saw and the standard reamer. In effect any oscillating equipment used in orthopedics, including the saw, reamer, drill, and the like may be made more precise in its ability to cut and prepare bone with the addition of ultrasonic energy. This may feel dangerous and counterintuitive to some, however, the surgeon typically applies a moderate amount of manual pressure to the saw and reamers, without being aware, which occasionally causes tremendous skiving, bending and eccentric reaming. An instrument that does not requires the surgeon's manual force maybe significantly safer and as well as more precise and effective.

A further option includes disposition of a sensor in the shaft of the ultrasonic reamers and saws so that the surgeon can ascertain when hard versus soft bone is being cut, adding a measure of safety by providing a visual numerical feedback as to the amount of pressure being utilized. This improvement (the ability to cut hard and soft bone with equal efficacy) will have tremendous implications in orthopedic surgery. When the acetabular cavity is prepared more precisely, with significantly lower tolerances, especially when directionality is observed, the acetabular implant (cup) may more easily follow the intended sinking path.

Other applications of this concept could be very useful. Pressfit and ingrowth fixation in total knee replacements in particular (as well as ankle, shoulder and other joints to a lesser degree) are fraught with problems, particularly that of inconsistent bony ingrowth and fixation. The fact that a surgeon is unable to obtain precise cuts on the bone may be a significant factor in why the bone ingrowth technology has not gotten off the ground in joints other than the hip. The problem is typically blamed on the surgeon and his less than perfect hands. The experienced surgeon boasts that only he should be doing this operation (i.e. non-cemented total knee replacement). This concept (a more precise saw that cuts hard and soft bone equally allowing lower tolerances) has huge potential in orthopedics, in that it can lead to elimination of the use of cement in orthopedic surgery altogether. This can spark off the growth and use of bone ingrowth technology in all aspects of joint replacement surgery which can lead to tremendous time saving in the operating room and better results for the patients.

In addition to the incorporated parent applications, embodiments of the present invention may include aspects of resistive force measurement, resistive force curves, and BMD tools that include force sensing, such as described in U.S. patent application Ser. No. 15/234,782 filed 11 Aug. 2016 which claims benefit of the incorporated '434 parent application as well as U.S. Patent Application No. 62/355,657 and U.S. Patent Application No. 62/353,024 and also described in U.S. patent application Ser. No. 15/284,091, all of which are hereby expressly incorporated by reference thereto in their entireties for all purposes.

These applications include a description of a resistive force for insertion of a hemispherical acetabular cup into an under reamed cavity. This resistive force is sometimes referred to as the FR curve, defining a "cup print" for the insertion parameters. This resistive force has been described as being variable with three distinct sections. It has a profile that may be described as an "exponential curve". There is an identification of an early section/part of this FR curve where poor insertion and pull out forces exist. There is an identification of a middle section (a sweet spot) on this FR curve where good insertion and extraction forces are achieved. And, finally, the discussion describes that using larger forces beyond the sweet spot provide little additional benefit to the strength of fixation, and may increase a risk of fracture. In one analogy, this FR curve may represent a dangerous peak such as Mount Everest having five base camps. In the discussion, there is an observation that an orthopedic surgeon should be content to stop at base camp 3 or 4, and perhaps should not attempt to summit, when trying to obtain press fit fixation of the cup in an under-reamed cavity. This phenomena has been described in association with BMD3 and BMD4.

There is a very serious problem in orthopedics. Some of the incorporated patent applications discuss trunnionosis in connection with material regarding "BMD4" and "Intelligent Prosthesis Two". There are fundamental problems related to truniosis in orthopedics, specifically on the insertion of a femoral and humeral head onto the trunnion and the related problems that have been so far described as tribo-corrosion. There many who believe that the mechanism of taper corrosion is best characterized as mechanically assisted crevice corrosion. Fretting initialed crevice corrosion in tapers is a complex problem and the severity is dependent on multiple factors. Corrosion has been associated with clinical complications, such as elevated metal ion levels, persistent pain, tissue damage, and early implant failure.

Regardless of the design, including shorter and slimmer trunnions and larger heads, as well as taper angles (including positive and negative mismatch) there appears to be some universal problems with the process of head impaction onto the trunnion that have to do with "taper impaction technique" and the "engagement of the modular taper interface" that doom the trunnion interface to failure.

Described herein are problems associated with head/trunnion impaction and possible solutions. Vibratory insertion of a prosthetic acetabular cup is extended here in that some of the same fundamental problems associated with mallet based impaction techniques of the prosthetic acetabular cup are present here with head/trunnion impaction.

Noted below are four specific and fundamental problems with current techniques of head to trunnion impaction:

A) Inconsistent magnitude of force. The force is delivered by a surgeon using a mallet. There is no standardization of magnitude of force. There is no guidance as to how much force needs to be delivered. The medical device companies have not done In Vitro studies to determine how much force to deliver for a good seal. There is no a priori information as to what type of force produces a desired "cold weld", which appears to be what we need to accomplish strong fixation with no micro-motion.

B) Inconsistent direction of force. Non-axial alignment of force is the norm for head to trunnion impaction. This produces "canting" which leads to micro motion and corrosion.

C) Impacting against a soft object. The impact is not "elastic" but "inelastic" or plastic. The kinetic energy produced by the surgeon and the mallet is mostly lost in a system that is inelastic. Momentum is conserved in that much of the energy produced by the surgeon and the hammer is dissipated by the spring like quality of the whole leg/femur/thigh/prosthesis complex. But kinetic energy is not conserved, with most of the energy lost by the system described above, and therefore, the transfer of energy from the head to trunnion interface is highly inefficient.

D) Assuming a surgeon is able to get the right amount (magnitude) of force delivered with the right technique (perfectly axially), How do you know you have actually achieved a "cold weld"? How do you know when to stop application of Force? No In Vitro studies have ever been done to guide the surgeon as to how much force to apply. Also, a proper tool have never been provided to the surgeon to accomplish this job.

The solution may include a new design with several key features.

1) A head may include a flat edge that allows it to sit flat on a table. A "head holder" may grasp the head in a 'normal' fashion on the flat edges. On an opposite side of the head holder a center axis point may be created, which allows ONLY central axis application of force.

2) The force as will be described can be delivered dynamically through controlled impaction as with BMD4 technique (e.g., various slide hammer configurations), or vibratory insertion as with BMD3 techniques or with Constant insertion (to allow the system to mostly deal with friction (e.g., a coefficient of kinetic friction Uk).

3) The prosthesis may have either indentations, holes, or ridges created in it to allow an insertion apparatus (BMD5) to purchase and grasp the prosthesis. This is a way to avoid unnecessary loss and waste of kinetic energy.

4) A force sensor/torque wrench/strain gauge within the tool measures the force experienced within the tool/head/trunnion/prosthesis complex.

5) An amount (magnitude) of force required to obtain a perfect weld can be determined in vitro. The force can be delivered with controlled impaction, vibratory insertion, or constant insertion. The force sensor may, in some implementations, act much like a torque wrench (possibly) stopping the application of the perfectly tuned force (both magnitude and direction) when a cold weld is obtained. Little to no dissipation of force/energy may occur in this system. The inconsistencies that are introduced by the surgeon and the mallet with current techniques are eliminated entirely. Since the surgeon is told in advance how much force to deliver and given the proper tool to accomplish this job, it is impossible to deliver less than required force. Since the tool only applies perfectly axial force, no canting can occur. Since the head and trunnion are now coupled/constrained in one physical system, wasting of kinetic energy will reduced or eliminated. The insertion of the head onto the trunnion is now done with a technologically intelligent and reliable system.

Figure 14:
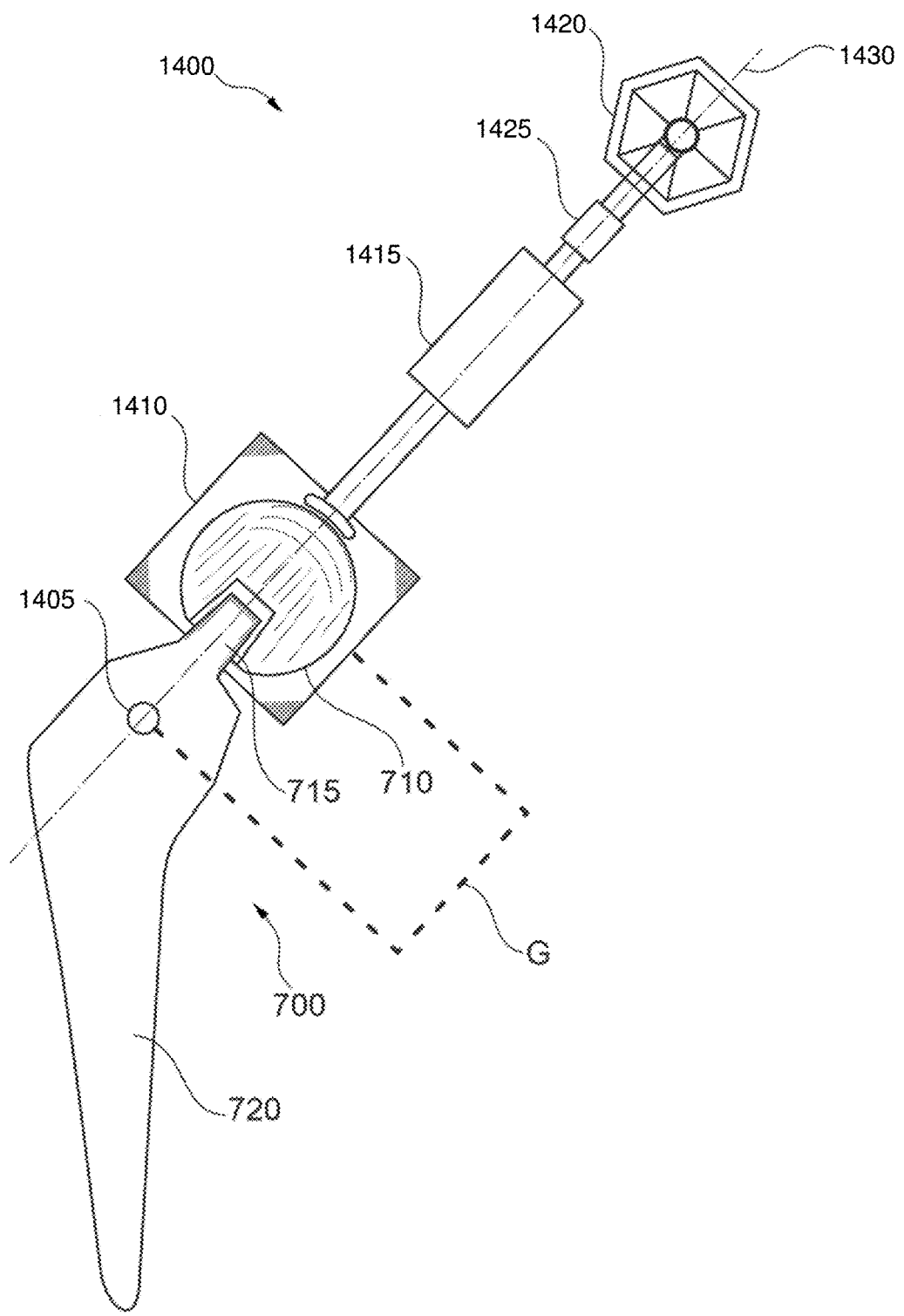
FIG. 14 illustrates a first embodiment for a BMD5 tool.
Figure 15:
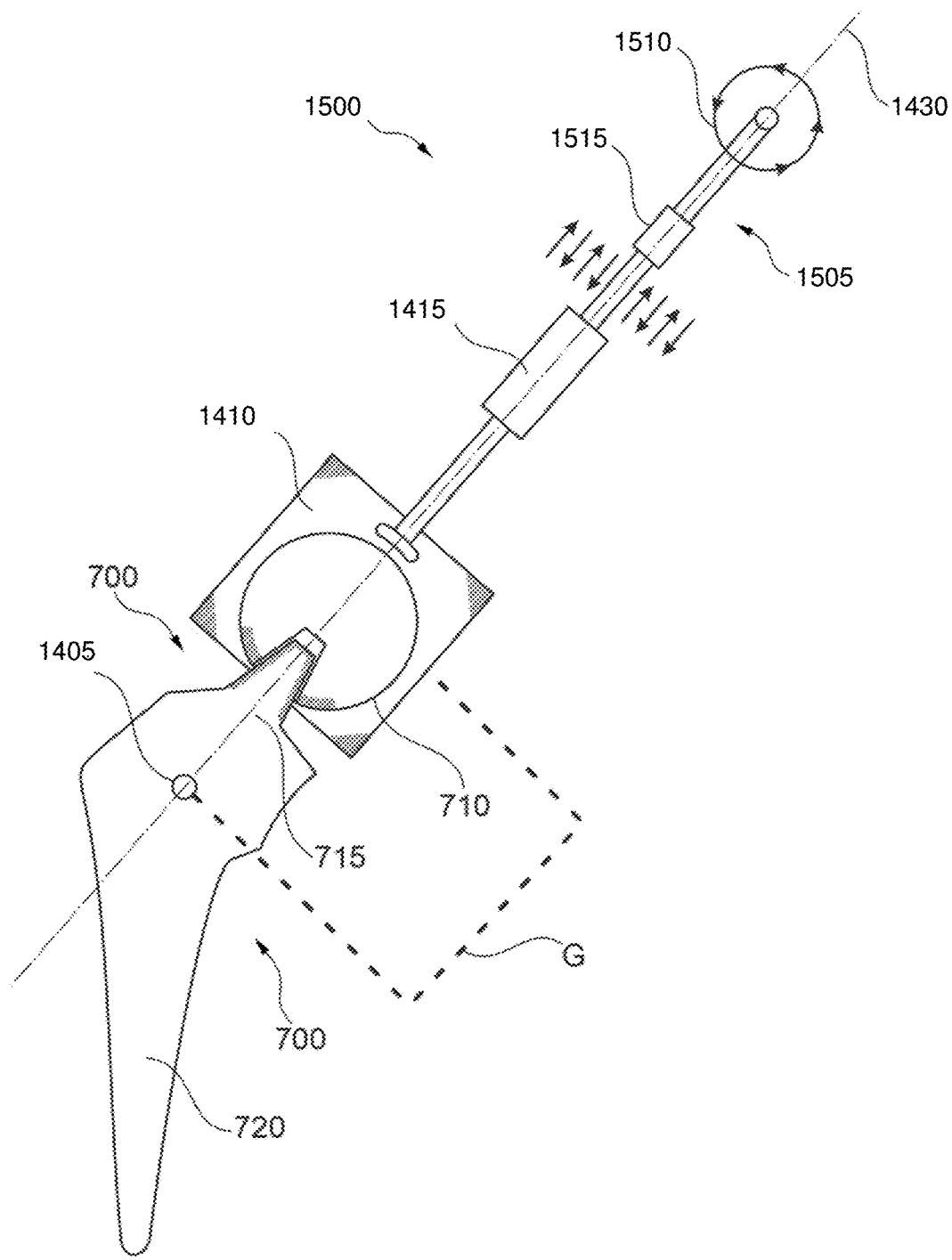
FIG. 15 illustrates a second embodiment for a BMD5 tool.
Figure 16:
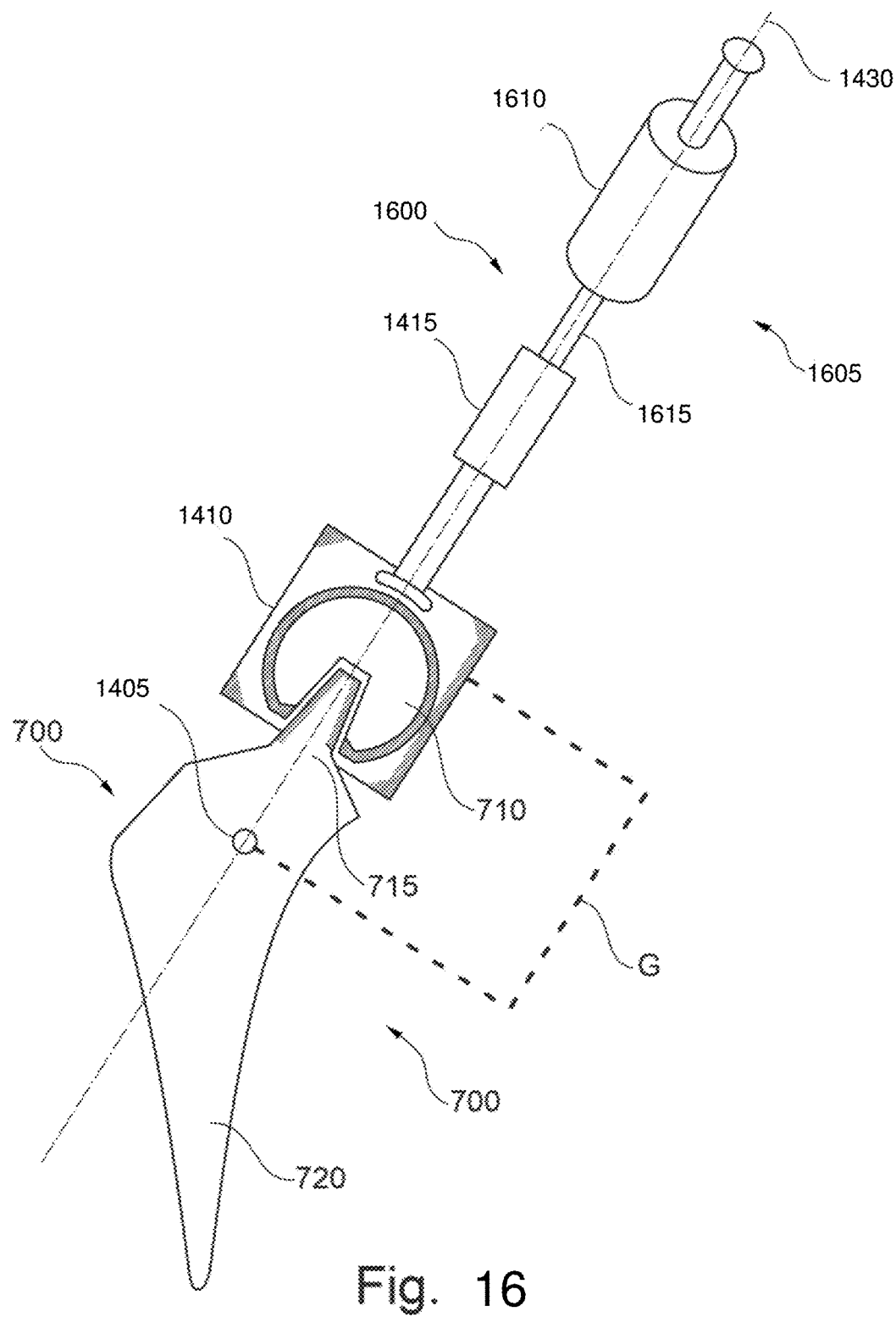
FIG. 16 illustrates a third embodiment for a BMD5 tool.

In each of FIG. 14-FIG. 16, an embodiment of a BMD5 tool will be used to help assemble a modular prosthesis. This is similar to the discussion of FIG. 7. In FIG. 7, modular prosthesis 700 was assembled using assembly tool 705 while in these discussions, a BMD5 tool replaces tool 705 (with an optional modification to prosthesis 700). Prosthesis 700 includes a head 710 and a trunnion taper 715 at an end of a stem 720 (e.g., a femoral stem for supporting a ball head to fit within an acetabular cup used in a total hip replacement procedure). During some embodiments of this alternative procedure, the surgeon assembles prosthesis 700 by using a BMD5 tool. The surgeon uses the BMD5 tool to drive, and cold weld, head 710 onto trunnion taper 715.

FIG. 14 illustrates a first embodiment for a BMD5 tool 1400 used in cooperation with assembly of modular prosthesis 700 to install head 710 onto trunnion taper 715 at an end of stem 720. Prosthesis 700 is modified to include a grip structure 1405 (e.g., an indentation, hole, cavity, aperture, and the like) to allow engagement of a retention structure (e.g., a claw, grasper, gripper, and the like—represented by G) coupled to both tool 1400 and to prosthesis 700. Optional grip structure 1405 may be used to reduce or eliminate wasting of kinetic energy during assembly and welding of head 710 onto taper 715.

BMD5 tool 1400 includes a head grasper 1410, an in-line force sensor module 1415, a torquer 1420, and torque converter 1425. Head grasper 1410 retains and aligns head 710 into an optimum installation orientation (e.g., perpendicular/normal) to allow application of force only along an assembly axis 1430 joining, and aligned with, grip structure 1405, head 710, taper 715, grasper 1410, module 1415 and torque converter 1425. This alignment allows for only force application only along assembly axis 1430 which prevents/reduces canting. Gripper G is illustrated as being functionally connected to grasper 1410, but could be mechanically communicated to another portion or component of tool 1400. This is a functional representation as there may be several mechanical ways to implement this function, including allowing relative displacement of the grasper and trunnion while maintaining the desired alignment(s).

Grasper 1410 is important in positioning (including alignment and relative orientation) of head 710 and trunnion 715. Head 710 includes an aperture, typically complementary to the taper of a mating surface of trunnion 715. Grasper 1410 secures head 710 for assembly in a very simple and efficient manner that positions, without relative canting, head 710 and trunnion 715.

Module 1415 may include a torque wrench/strain gauge allowing a surgeon to understand one or more forces in play, such as knowing exactly how much force needs to be, and is being, delivered to obtain perfect cold weld of head 710 onto taper 715.

Torquer 1420 may include a manual or motorized source of force or torque, such as a torque engine which may include a rotary motor.

Torque converter 1425 transforms torque of torquer 1420 into axial-exclusive linear force for module 1415. When the torque engine provides rotary force, converter 1425 may include a linear motion converter to alter the rotary force into an axially-aligned linear force.

In operation, femoral head 710 may be joined to trunnion taper 715 using constant insertion. That is, head 710 is "press-fit" with a constant (but potentially variable) axial force. This is distinguished from application of one or more discrete impacts or impulses onto grasper 1410. Constant insertion strongly implicates Uk (coefficient of kinetic friction) which may be less than a series of discrete impacts that more strongly implicate a coefficient of static friction. In some cases, stem 720 is installed into bone and thereafter tool 1400 is used to install head 710 onto the taper of trunnion 715 to obtain a sufficient mechanical connection. Herein, that mechanical connection is sometimes referred to as a "cold weld" which for purposes of this application means that head 710 and trunnion 715 are engaged enough that relative micro-motion is eliminated or sufficiently reduced that risks of relative micro-motion are reduced below a predetermined threshold.

This is one aspect of the present invention, that a manufacturer of modular prosthetics may develop, or share, information on the forces necessary to produce a cold weld as noted above. Without recognition of the problems noted herein and a BMD5 tool to measure and/or control assembly forces and a surgeon swinging uncalibratingly a mallet to freely strike head 710 and drive it onto trunnion 715, there was insufficient need or motivation to develop or share this type of information.

FIG. 15 illustrates a second embodiment for a BMD5 tool 1500 used in cooperation with assembly of modular prosthesis 700 to install head 710 onto trunnion taper 715 at an end of stem 720. Tool 1500 varies from tool 1400 in that tool 1500 performs insertion using a vibration profile. The vibration profile is provided by a vibration engine 1505 that may include a rotary motor 1510 coupled to a linear motion converter 1515 to impart a vibration to head grasper 1410 (and then to head 710) to insert and cold weld head 710 onto trunnion taper 715. There are other ways to implement vibration engine 1505.

In operation, tool 1500 may join head 710 to taper 715 with a vibratory force (implicating a blend of static and kinetic coefficients of friction—Us and Uk), which may require less force than a series of discrete/dynamic impacts onto head 710.

FIG. 16 illustrates a third embodiment for a BMD5 tool 1600 used in cooperation with assembly of modular prosthesis 700 to install head 710 onto trunnion taper 715 at an end of stem 720. Tool 1600 varies from tool 1400 in that tool 1600 performs insertion using an impact profile. The impact profile is provided by an impact engine 1605 that may include a slide hammer 1610 having an axially-limited sliding mass to impart a discrete impact onto a shaft 1615 and by that mechanism to head grasper 1410 (and then to head 710) to insert and cold weld head 710 onto trunnion taper 715. There are other ways to implement impact engine 1605, including manual, mechanized (e.g., robotic), and semi-mechanized solutions.

In operation, tool 1600 may join head 710 to taper 715 with a series of one or more discrete impacts from impact engine 1605 (implicating predominantly/exclusively static coefficient of friction Us).

In summary BMD5 is a tool that:

1. Advantageously modifies a femoral prosthesis in such a way to allow a grasp or engagement of the prosthesis by the BMD5 tool. This can be accomplished in a variety of ways: A hole, dent, ridges, and indentations can be created on the prosthesis. The ability to grasp the prosthesis is important in some embodiments in that it prevents, or reduces, waste of kinetic energy.

2. The BMD5 tool may include a "head grasper" which holds the femoral or humeral head in a perpendicular or "normal" fashion. This allows the force of insertion/impaction to be applied perfectly axially, without the risk of "canting".

3. The BMD5 tool has a torque wrench/strain gauge/force sensor of a wide variety of possible types that measures an amount of force applied through the tool/head/trunnion/prosthesis complex. The surgeon will always know exactly how much force is being applied. The amount of force required to obtain a perfect "cold weld" can be predetermined in the laboratory. The surgeon can simply apply the force that is recommended by the medical device company to obtain a perfect cold weld every single time, eliminating all variability that is currently present with application of force with variable surgeon strengths and mallet sizes.

4. For Constant insertion, manual or motorized rotatory motion is converted into linear motion with any linear motion converter. In a simple form, the rotatory motion of a screw/thread is converted into linear compression. For Vibratory insertion, similarly, rotatory motion by a motor is converted into linear vibration. For Discrete Impacts a sliding mass of known weight can travel over a known distance to deliver a predetermined amount of force.

BMD5 may include a self-contained system that reduces any wasting of energy. BMD5 may allow for perfect axial delivery of force while providing for quantitative measurement of applied/communicated/transmitted force(s). So stakeholders can rest assured that every step has been taken to obtain a cold weld at the trunnion/head interface. Embodiments of BMD5 may allow a surgeon to cold weld the femoral head onto the trunnion simply, efficiently, and accurately while minimizing risks of improper installation. Some embodiments of BMD5 may include ultrasonic press-fitting, such as described in Csaba LAURENCZY et al., "ULTRASONIC PRESS-FITTING: A NEW ASSEMBLY TECHNIQUE" S. Ratchev (Ed.): IPAS 2014, IFIP AICT 435, pp. 22-29, 2014, hereby expressly incorporated by reference in its entirety for all purposes.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A system for assembly of a modular prosthesis including a stem portion, a trunnion portion coupled to the stem portion, the trunnion portion having an insertion profile defining a trunnion axis, and a prosthesis head configured for an installation on the trunnion portion and the prosthesis head defining a distal head portion, a proximal head portion opposite of the distal head portion, the prosthesis head further defining a bore with the proximal head portion including a bore opening into the bore, the bore complementary to the insertion profile with the bore defining a bore axis, comprising:
    a head alignment structure including a housing defining a cavity complementary to an outer portion of the prosthesis head with said housing having a head alignment axis extending through said cavity wherein said housing is configured to anti-rotatingly enclose, during the installation, the prosthesis head within said cavity and configured to align said head alignment axis with the bore axis producing and maintaining a head alignment of said head alignment axis with the bore axis:
    wherein said housing engages both the distal head portion and the proximal head portion.

2. The system of claim 1 further comprising:
    a trunnion engagement structure configured to be coupled to the trunnion portion and disposed on the trunnion axis; and
    an alignment bracket including a first bracket engagement structure complementary to said trunnion engagement structure and including a second bracket engagement structure complementary to said head alignment structure; and
    wherein said alignment bracket is configured to secure said head alignment structure relative to the trunnion portion while aligning said head alignment axis with the trunnion axis.

3. The system of claim 1 further comprising:
    a tool, configured to engage said head alignment structure, said tool further configured to generate an assembly force along an assembly force axis, said assembly force axis aligned with said head alignment axis when said head alignment axis is aligned with said trunnion axis.

4. The system of claim 2 further comprising:
    a tool, configured to engage said alignment bracket, said tool further configured to generate an assembly force along an assembly force axis, said assembly force axis aligned with said head alignment axis when said alignment bracket secures said head alignment structure relative to the trunnion portion and when alignment bracket aligns said head alignment axis with the trunnion axis.

5. The system of claim 3 wherein said tool includes a shaft coupling said head alignment structure and wherein said shaft includes a force sensor.

6. The system of claim 4 wherein said tool includes a shaft for coupling to said head alignment structure and wherein said shaft includes a force sensor.

7. The system of claim 3 wherein said tool includes a force engine configured to produce said assembly force.

8. The system of claim 7 wherein said force engine includes a torquer configured to generate a torque and a converter coupled to said torquer configured to produce a decreasing displacement, responsive to said torque, of the prosthesis head relative to the stem.

9. The system of claim 7 wherein said force engine includes a motor configured to generate a motion and a converter coupled to said motor configured to produce a decreasing linear displacement, responsive to said motion, of the prosthesis head relative to the stem.

10. The system of claim 7 wherein said force engine includes an impulser configured to generate a set of impulses and a converter coupled to said impulser configured to produce a decreasing linear displacement, responsive to said set of impulses, of the prosthesis head relative to the stem.

11. The system of claim 4 wherein said tool includes a force engine configured to produce said assembly force.

12. The system of claim 11 wherein said force engine includes a torquer configured to generate a torque and a converter coupled to said torquer configured to produce a decreasing displacement, responsive to said torque, of the prosthesis head relative to the stem.

13. The system of claim 11 wherein said force engine includes a motor configured to generate a motion and a converter coupled to said motor configured to produce a decreasing linear displacement, responsive to said motion, of the prosthesis head relative to the stem.

14. The system of claim 11 wherein said force engine includes an impulser configured to generate a set of impulses and a converter coupled to said impulser configured to produce a decreasing linear displacement, responsive to said motion, of the prosthesis head relative to the stem.

15. The system of claim 5 wherein said tool includes a force engine configured to produce said assembly force.

16. The system of claim 15 wherein said force engine includes a torquer configured to generate a torque and a converter coupled to said torquer configured to produce a decreasing displacement, responsive to said torque, of the prosthesis head relative to the stem.

17. The system of claim 15 wherein said force engine includes a motor configured to generate a motion and a converter coupled to said motor configured to produce a decreasing linear displacement, responsive to said motion, of the prosthesis head relative to the stem.

18. The system of claim 15 wherein said force engine includes an impulser configured to generate a set of impulses and a converter coupled to said impulser configured to produce a decreasing linear displacement, responsive to said motion, of the prosthesis head relative to the stem.

19. The system of claim 6 wherein said tool includes a force engine configured to produce said assembly force in realtime during application of said assembly force to said head alignment structure.

20. The system of claim 19 wherein said force engine includes a torquer configured to generate a torque and a converter coupled to said torquer configured to produce a decreasing displacement, responsive to said torque, of the prosthesis head relative to the stem.

21. The system of claim 19 wherein said force engine includes a motor configured to generate a motion and a converter coupled to said motor configured to produce a decreasing linear displacement, responsive to said motion, of the prosthesis head relative to the stem.

22. The system of claim 19 wherein said force engine includes an impulser configured to generate a set of impulses and a converter coupled to said impulser configured to produce a decreasing linear displacement, responsive to said motion, of the prosthesis head relative to the stem.

23. The system of claim 3 wherein the prosthesis head and the trunnion have a predetermined cold weld point wherein an application of a joining force in excess of said predetermined cold weld point produces a cold weld of the prosthesis head to the trunnion portion and wherein said tool generates said assembly force exceeding said predetermined cold weld point when said head alignment axis is aligned with said trunnion axis.

24. A system for assembly of a modular prosthesis including a stem portion, a trunnion portion coupled to the stem portion, the trunnion portion having an insertion profile defining a trunnion axis, and a prosthesis head configured to be installed on the trunnion portion and defining a bore complementary to said insertion profile with the bore defining a bore axis, comprising:

a head alignment structure including a housing defining a cavity complementary to an outer portion of the prosthesis head with said housing having a head alignment axis extending through said cavity wherein said housing is configured to secure the prosthesis head within said cavity and align said head alignment axis with the bore axis producing a head alignment of said head alignment axis and said bore axis, further comprising:

a tool, configured to engage said head alignment structure, said tool further configured to generate an assembly force along an assembly force axis, said assembly force axis aligned with said head alignment axis when said head alignment axis is aligned with said trunnion axis:

wherein said generation of said assembly force is configured to mechanically join the prosthesis head and the trunnion portion with a pressfit fixation and wherein said assembly force includes an application of ultrasonic energy during engagement of the prosthesis head and the trunnion portion with said pressfit fixation.

25. The system of claim 24 wherein said assembly force further includes, concurrent with said application of ultrasonic energy, an application of non-ultrasonic energy during engagement of the prosthesis head and the trunnion portion with said pressfit fixation.

26. The system of claim 1 wherein the prosthesis head includes a spheroidal bearing surface for articulation with a corresponding joint surface, and an assembly surface defining the bore receiving the trunnion portion wherein the bore axis extends at a predetermined angle relative to said assembly surface, and in which there is a discontinuity at an interface between said spheroidal bearing surface and said assembly surface, said assembly surface being arranged on a plane which is parallel to, or contains, a plane which is defined by an opening to the bore in the prosthesis head when the prosthesis head is viewed from one side in cross-section, and wherein said cavity of said head alignment structure includes an alignment surface complementary to said assembly surface and configured to configure and constrain said head alignment when the prosthesis head is installed into said cavity.

27. The system of claim 26 wherein said predetermined angle is about ninety degrees.

28. The system of claim 3 wherein said head alignment structure includes a tool engagement system, said tool engagement system configured to secure said tool to said head alignment structure with said assembly force axis aligned with said head alignment axis.

29. The system of claim 4 wherein said head alignment structure includes a tool engagement system, said tool engagement system configured to secure said tool to said head alignment structure with said assembly force axis aligned with said head alignment axis.

30. The system of claim 1 wherein the distal head portion includes a spherical segment, wherein the proximal head portion includes a planar surface, and wherein the housing engages both said spherical segment and said planar surface.

31. The system of claim 1 wherein the distal portion and the planar portion cooperatively define an anti-rotation indexing structure and wherein said housing is configured to engage said anti-rotation indexing structure producing a rotation inhibition of the prosthesis head within said cavity.

32. The system of claim 20 wherein said spherical segment and said planar surface cooperatively define an anti-rotation indexing structure, said anti-rotation indexing structure configured to inhibit a rotation of the prosthesis head within said cavity when enclosed by said housing.

* * * * *